US011812816B2

(12) United States Patent
Gardner et al.

(10) Patent No.: US 11,812,816 B2
(45) Date of Patent: Nov. 14, 2023

(54) PROTECTIVE HEADWEAR WITH AIRFLOW

(71) Applicant: ILLINOIS TOOL WORKS INC., Glenview, IL (US)

(72) Inventors: William P. Gardner, Appleton, WI (US); Nishank R. Patel, Appleton, WI (US); Eric T. Sommers, Appleton, WI (US); John C. Mehnert, Madison, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 15/592,491

(22) Filed: May 11, 2017

(65) Prior Publication Data
US 2018/0325205 A1 Nov. 15, 2018

(51) Int. Cl.
*A42B 3/28* (2006.01)
*A61F 9/06* (2006.01)
(Continued)

(52) U.S. Cl.
CPC ............. *A42B 3/286* (2013.01); *A42B 3/085* (2013.01); *A42B 3/283* (2013.01); *A42B 3/324* (2013.01);
(Continued)

(58) Field of Classification Search
CPC ......... A42B 3/286; A42B 3/085; A42B 3/283; A42B 3/324; A42B 3/281; F41H 1/04;
(Continued)

(56) References Cited

U.S. PATENT DOCUMENTS

| 716,505 A | 12/1902 | Williams |
| 716,506 A | 12/1902 | Williams |

(Continued)

FOREIGN PATENT DOCUMENTS

| CN | 101056677 A | 10/2007 |
| CN | 101795645 A | 8/2010 |

(Continued)

OTHER PUBLICATIONS

International Search Report and Written Opinion issued for EP PCT/US2018/030469 dated Sep. 14, 2018, 20 pages.
(Continued)

*Primary Examiner* — Khoa D Huynh
*Assistant Examiner* — Aiying Zhao
(74) *Attorney, Agent, or Firm* — McAndrews, Held & Malloy, Ltd.

(57) ABSTRACT

In one aspect, a protective headwear is provided and includes a headgear, an outer shell, a duct and a manifold. The headgear is configured to engage a wearer's head and at least partially support the protective headwear on a wearer's head. The headgear includes a front, a rear opposite the front, a right side, and a left side opposite the right side. The outer shell is coupled to the headgear at a coupling location and includes a shield positioned to the front of the headgear. The duct is at least partially coupled to and at least partially positioned in an interior of the outer shell. The duct is located below the coupling location. The manifold is positioned to the rear of the headgear and configured to divert airflow into at least a first portion of airflow and a second portion of airflow

33 Claims, 19 Drawing Sheets

(51) Int. Cl.
*F41H 1/04* (2006.01)
*A42B 3/32* (2006.01)
*A42B 3/08* (2006.01)

(52) U.S. Cl.
CPC .............. *A61F 9/067* (2013.01); *A61F 9/068* (2013.01); *F41H 1/04* (2013.01)

(58) Field of Classification Search
CPC ........ A61F 9/068; A61F 9/067; A62B 18/006; A41D 13/11
See application file for complete search history.

(56) References Cited

U.S. PATENT DOCUMENTS

| | | | |
|---|---|---|---|
| 2,085,249 A | 6/1937 | Bullard | |
| 2,402,820 A | 6/1946 | Kitchen | |
| 3,112,745 A | 12/1963 | Boyer | |
| 3,119,279 A * | 1/1964 | Reece | F16K 35/02 |
| | | | 74/528 |
| 3,390,514 A | 7/1968 | Raschke | |
| 3,584,314 A * | 6/1971 | Hobson | A61F 9/068 |
| | | | 128/205.25 |
| 3,629,868 A | 12/1971 | Greenlee | |
| 3,668,362 A | 6/1972 | Kirchner et al. | |
| 3,685,512 A | 8/1972 | Raschke | |
| 3,724,740 A | 4/1973 | Imamura et al. | |
| 3,881,478 A | 5/1975 | Rosendahl | |
| 3,914,796 A * | 10/1975 | Barta | A61F 9/06 |
| | | | 2/8.3 |
| 3,927,668 A | 12/1975 | Raschke | |
| 3,943,573 A | 3/1976 | Budmiger | |
| 4,011,865 A * | 3/1977 | Morishita | A62B 18/00 |
| | | | 128/201.15 |
| 4,031,564 A | 6/1977 | Wood | |
| 4,052,984 A | 10/1977 | Brockway | |
| 4,080,664 A | 3/1978 | Morris et al. | |
| 4,149,908 A | 4/1979 | Thall et al. | |
| 4,172,294 A | 10/1979 | Harris | |
| 4,185,329 A | 1/1980 | Sarazen | |
| 4,236,514 A | 12/1980 | Moretti | |
| 4,271,833 A | 6/1981 | Moretti | |
| 4,309,774 A | 1/1982 | Guzowski | |
| 4,335,472 A | 6/1982 | Rappleyea | |
| 4,452,240 A | 6/1984 | Moretti | |
| 4,455,683 A | 6/1984 | Moretti | |
| 4,464,800 A | 8/1984 | Edwards | |
| 4,484,575 A | 11/1984 | Brockway et al. | |
| 4,513,452 A | 4/1985 | Rankin, Sr. | |
| 4,542,538 A | 9/1985 | Moretti et al. | |
| 4,556,991 A | 12/1985 | Margaronis | |
| 4,561,162 A | 12/1985 | Brockway et al. | |
| 4,576,669 A | 3/1986 | Caputo | |
| 4,619,254 A | 10/1986 | Moretti et al. | |
| 4,649,571 A | 3/1987 | Falkiner | |
| 4,672,968 A | 6/1987 | Lenox | |
| 4,694,141 A | 9/1987 | Hahn | |
| 4,697,058 A | 9/1987 | Mueller | |
| 4,721,517 A | 1/1988 | Cloutier | |
| 4,726,104 A | 2/1988 | Foster et al. | |
| 4,867,770 A | 9/1989 | Feeney | |
| 4,875,235 A | 10/1989 | Kuhlman | |
| 4,883,547 A | 11/1989 | Japuntich | |
| 4,890,335 A | 1/1990 | Crowson | |
| 4,899,740 A | 2/1990 | Napolitano | |
| 4,937,879 A | 7/1990 | Hall | |
| 4,988,342 A | 1/1991 | Herweck et al. | |
| 4,989,598 A | 2/1991 | Berg et al. | |
| 5,029,342 A | 7/1991 | Stein et al. | |
| 5,031,237 A | 7/1991 | Honrud | |
| 5,088,115 A | 2/1992 | Napolitano | |
| 5,123,114 A | 6/1992 | Desanti | |
| 5,154,712 A | 10/1992 | Herweck et al. | |
| 5,189,735 A | 3/1993 | Corona | |
| 5,191,468 A | 3/1993 | Mases | |
| 5,351,151 A | 9/1994 | Levy | |
| 5,357,951 A | 10/1994 | Ratner | |
| 5,464,010 A | 11/1995 | Byram | |
| 5,549,104 A | 8/1996 | Bullard | |
| 5,555,879 A | 9/1996 | Helin | |
| 5,561,855 A | 10/1996 | Mcfall | |
| 5,645,056 A | 7/1997 | Pomeroy | |
| 5,749,096 A | 5/1998 | Fergason et al. | |
| 5,896,579 A | 4/1999 | Johnson | |
| 5,924,420 A | 7/1999 | Reischel et al. | |
| 5,954,055 A | 9/1999 | Miyake | |
| 5,991,072 A | 11/1999 | Solyntjes et al. | |
| 6,012,452 A | 1/2000 | Pagan | |
| 6,070,579 A | 6/2000 | Bryant et al. | |
| 6,102,033 A | 8/2000 | Baribeau | |
| 6,119,692 A | 9/2000 | Byram | |
| 6,148,817 A | 11/2000 | Bryant et al. | |
| 6,260,197 B1 | 7/2001 | Hoogewind | |
| 6,260,917 B1 | 7/2001 | Marechal | |
| 6,290,642 B1 | 9/2001 | Reinhard et al. | |
| 6,298,498 B1 | 10/2001 | Burns | |
| 6,325,754 B1 | 12/2001 | Reinhard et al. | |
| 6,370,748 B1 | 4/2002 | Baccini | |
| 6,465,102 B1 | 10/2002 | Honigfort et al. | |
| 6,591,837 B1 | 7/2003 | Byram | |
| 6,598,236 B1 | 7/2003 | Gantt | |
| 6,609,516 B2 | 8/2003 | Hollander et al. | |
| 6,637,091 B2 | 10/2003 | Halstead et al. | |
| 6,715,489 B2 | 4/2004 | Bostock et al. | |
| 6,715,490 B2 | 4/2004 | Byram | |
| 6,763,830 B1 | 7/2004 | Davis et al. | |
| 6,902,774 B2 | 6/2005 | Nicolussi | |
| 6,911,108 B2 | 6/2005 | Sarmiento | |
| 6,973,672 B2 | 12/2005 | Huh | |
| 6,973,676 B1 | 12/2005 | Simpson | |
| 7,000,262 B2 | 2/2006 | Bielefeld | |
| 7,043,772 B2 | 5/2006 | Bullard | |
| 7,069,930 B2 | 7/2006 | Bostock et al. | |
| 7,093,302 B1 | 8/2006 | Burns | |
| 7,150,047 B2 | 12/2006 | Fergason | |
| 7,156,093 B2 | 1/2007 | Bullard | |
| 7,188,622 B2 | 3/2007 | Martin et al. | |
| 7,213,271 B1 | 5/2007 | Bielefeld | |
| 7,284,281 B2 | 10/2007 | Huh | |
| 7,308,719 B2 | 12/2007 | Huh | |
| 7,318,437 B2 * | 1/2008 | Gunaratnam | A61M 16/0666 |
| | | | 128/206.11 |
| 7,358,458 B2 | 4/2008 | Daniel | |
| 7,393,712 B2 | 7/2008 | Smith et al. | |
| 7,410,095 B2 | 8/2008 | Selover | |
| 7,454,800 B2 | 11/2008 | Taylor et al. | |
| 7,493,900 B1 | 2/2009 | Japuntich et al. | |
| 7,644,478 B2 | 1/2010 | Boyer | |
| 7,699,053 B1 | 4/2010 | Bullard | |
| 7,718,031 B2 | 5/2010 | Kang et al. | |
| 7,971,267 B2 | 7/2011 | Huh | |
| 8,015,970 B2 | 9/2011 | Klun et al. | |
| 8,087,254 B2 | 1/2012 | Arnold | |
| 8,104,094 B2 | 1/2012 | Uttrachi | |
| 8,171,933 B2 | 5/2012 | Xue et al. | |
| 8,286,634 B2 | 10/2012 | Madaus et al. | |
| 8,336,113 B2 | 12/2012 | Uttrachi | |
| 8,359,662 B2 | 1/2013 | Viljanen | |
| 8,365,732 B2 | 2/2013 | Johnstone | |
| 8,528,560 B2 | 9/2013 | Duffy | |
| 8,551,279 B2 | 10/2013 | Johnson et al. | |
| 8,640,704 B2 | 2/2014 | Spoo et al. | |
| 8,661,570 B2 | 3/2014 | Huh | |
| 8,679,853 B2 | 3/2014 | Bhullar et al. | |
| 8,684,004 B2 | 4/2014 | Eifler | |
| 8,932,424 B2 | 1/2015 | Johnson et al. | |
| 9,038,198 B2 | 5/2015 | Feinberg | |
| 9,706,805 B2 | 7/2017 | Pereira | |
| 9,956,118 B2 | 5/2018 | Sernfalt | |
| 2004/0262364 A1 | 12/2004 | Halstead et al. | |
| 2005/0012197 A1 | 1/2005 | Smith et al. | |
| 2005/0017641 A1 | 1/2005 | Kruger et al. | |
| 2005/0268907 A1 | 12/2005 | McFarlane | |
| 2006/0010551 A1 | 1/2006 | Bishop | |

(56) References Cited

U.S. PATENT DOCUMENTS

| | | |
|---|---|---|
| 2006/0101552 A1 | 5/2006 | Lee et al. |
| 2006/0107431 A1 | 5/2006 | Curran et al. |
| 2006/0201513 A1 | 9/2006 | Chu |
| 2006/0231100 A1 | 10/2006 | Walker et al. |
| 2007/0050892 A1* | 3/2007 | Charles .............. A61F 9/06 2/410 |
| 2007/0068529 A1 | 3/2007 | Kalatoor et al. |
| 2007/0088234 A1 | 4/2007 | Tseng |
| 2007/0089215 A1 | 4/2007 | Biche et al. |
| 2007/0113318 A1 | 5/2007 | Weston |
| 2007/0215254 A1 | 9/2007 | Birke et al. |
| 2007/0226881 A1 | 10/2007 | Reinhard et al. |
| 2007/0245467 A1 | 10/2007 | Lilenthal |
| 2008/0011303 A1 | 1/2008 | Angadjivand et al. |
| 2008/0095898 A1 | 4/2008 | Mansuino |
| 2008/0106001 A1 | 5/2008 | Slafer |
| 2008/0189820 A1 | 8/2008 | Duffy et al. |
| 2009/0031485 A1 | 2/2009 | Prusinski |
| 2009/0044808 A1 | 2/2009 | Guney et al. |
| 2009/0055987 A1* | 3/2009 | Becker .............. A61F 9/068 2/8.6 |
| 2009/0184099 A1 | 7/2009 | Eddington et al. |
| 2009/0210988 A1 | 8/2009 | Becker et al. |
| 2009/0210989 A1 | 8/2009 | Becker et al. |
| 2009/0235420 A1 | 9/2009 | Chiang |
| 2009/0277451 A1 | 11/2009 | Weinberg |
| 2009/0277462 A1 | 11/2009 | Garber et al. |
| 2009/0277814 A1 | 11/2009 | Hamerly et al. |
| 2009/0283096 A1 | 11/2009 | Cerbini |
| 2009/0298024 A1 | 12/2009 | Balzler |
| 2010/0154805 A1 | 6/2010 | Duffy et al. |
| 2010/0212058 A1 | 8/2010 | Wanhainen |
| 2010/0229286 A1* | 9/2010 | Ahlgren .............. A42B 3/142 2/416 |
| 2010/0287676 A1 | 11/2010 | Seo |
| 2011/0179541 A1 | 7/2011 | Wright |
| 2011/0226256 A1 | 9/2011 | Dubach |
| 2011/0266718 A1 | 11/2011 | Angadjivand et al. |
| 2012/0024289 A1 | 2/2012 | Johnstone et al. |
| 2012/0157904 A1 | 6/2012 | Stein |
| 2012/0184046 A1 | 7/2012 | Atkin |
| 2012/0246809 A1* | 10/2012 | Elam .............. A42B 3/286 2/424 |
| 2012/0260920 A1 | 10/2012 | Choi et al. |
| 2012/0286958 A1 | 11/2012 | Dunbar |
| 2012/0291172 A1 | 11/2012 | Wills |
| 2013/0111648 A1 | 5/2013 | Huh |
| 2013/0111653 A1 | 5/2013 | Huh |
| 2013/0220332 A1 | 8/2013 | Baska |
| 2013/0291876 A1 | 11/2013 | Angadjivand et al. |
| 2013/0305524 A1 | 11/2013 | Hohenthanner et al. |
| 2013/0312151 A1 | 11/2013 | North |
| 2014/0007312 A1 | 1/2014 | Wright |
| 2014/0007881 A1 | 1/2014 | Rummery et al. |
| 2014/0026897 A1 | 1/2014 | Saroch et al. |
| 2014/0110685 A1 | 4/2014 | Hong et al. |
| 2014/0166001 A1 | 6/2014 | Kooken |
| 2014/0168546 A1 | 6/2014 | Magnusson et al. |
| 2014/0182600 A1 | 7/2014 | Duffy |
| 2014/0190486 A1 | 7/2014 | Dunn et al. |
| 2014/0208476 A1 | 7/2014 | Chen |
| 2014/0224256 A1 | 8/2014 | Skov et al. |
| 2014/0260933 A1 | 9/2014 | Ardiff et al. |
| 2014/0332005 A1 | 11/2014 | Kunz et al. |
| 2015/0059771 A1 | 3/2015 | Duffy |
| 2015/0069036 A1 | 3/2015 | Farah |
| 2015/0264992 A1 | 9/2015 | Happel |
| 2015/0359680 A1* | 12/2015 | Gardner .............. A61F 9/068 2/8.6 |
| 2016/0183622 A1 | 6/2016 | Patel |
| 2017/0112226 A1 | 4/2017 | Watkins |

FOREIGN PATENT DOCUMENTS

| | | |
|---|---|---|
| CN | 101815556 A | 8/2010 |
| CN | 101827538 A | 9/2010 |
| CN | 102370541 A | 3/2012 |
| CN | 102525731 A | 7/2012 |
| CN | 102551956 A | 7/2012 |
| CN | 203264074 U | 11/2013 |
| CN | 104684426 A | 6/2015 |
| CN | 106572716 A | 4/2017 |
| CN | 106659589 A | 5/2017 |
| EP | 0269551 A2 | 6/1988 |
| EP | 0269589 A1 | 6/1988 |
| EP | 0309633 A1 | 4/1989 |
| EP | 0417026 A1 | 3/1991 |
| EP | 0582286 A1 | 2/1994 |
| EP | 0894443 A2 | 2/1999 |
| EP | 0911049 A1 | 4/1999 |
| EP | 0983190 A1 | 3/2000 |
| EP | 0983192 B1 | 3/2000 |
| EP | 1041865 A2 | 10/2000 |
| EP | 1061824 A1 | 12/2000 |
| EP | 1114871 A1 | 7/2001 |
| EP | 1506034 A2 | 2/2005 |
| EP | 1516645 A2 | 3/2005 |
| EP | 1699531 A1 | 9/2006 |
| EP | 1773148 A1 | 4/2007 |
| EP | 1800706 A1 | 6/2007 |
| EP | 1809386 A1 | 7/2007 |
| EP | 1847298 A1 | 10/2007 |
| EP | 1898735 A1 | 3/2008 |
| EP | 1951123 A1 | 8/2008 |
| EP | 2099532 A1 | 9/2009 |
| EP | 2298096 A2 | 3/2011 |
| EP | 2298419 A1 | 3/2011 |
| EP | 2314353 A1 | 4/2011 |
| EP | 2349426 A1 | 8/2011 |
| EP | 2477588 A1 | 7/2012 |
| EP | 2486815 A1 | 8/2012 |
| EP | 2589308 A1 | 5/2013 |
| EP | 2589309 A1 | 5/2013 |
| EP | 2630993 A1 | 8/2013 |
| EP | 2 907 401 A1 | 8/2015 |
| WO | 1984/003193 | 8/1984 |
| WO | 1986/003128 | 6/1986 |
| WO | 1989/000919 A1 | 2/1989 |
| WO | 1993/003636 A1 | 3/1993 |
| WO | 1993/018726 A1 | 9/1993 |
| WO | 1994/023680 A1 | 10/1994 |
| WO | 1995/025005 A1 | 9/1995 |
| WO | 1996/028217 A1 | 9/1996 |
| WO | 1998/006244 A1 | 2/1998 |
| WO | 1999/016508 A1 | 4/1999 |
| WO | 1999/045810 | 9/1999 |
| WO | 2000/003899 A2 | 1/2000 |
| WO | 2001/078839 A2 | 10/2001 |
| WO | 2002/002191 A1 | 1/2002 |
| WO | 2003/020438 A2 | 3/2003 |
| WO | 2003/068319 A1 | 8/2003 |
| WO | 2003/097145 A2 | 11/2003 |
| WO | 2003/097968 A1 | 11/2003 |
| WO | 2003/103425 A1 | 12/2003 |
| WO | 2004/035142 A1 | 4/2004 |
| WO | 2004/091726 A1 | 10/2004 |
| WO | 2004/106082 A1 | 12/2004 |
| WO | 2005/000411 A1 | 1/2005 |
| WO | 2005/002481 A1 | 1/2005 |
| WO | 2005/008275 A1 | 1/2005 |
| WO | 2005/065780 A1 | 7/2005 |
| WO | 2006/019472 A1 | 2/2006 |
| WO | 2006/026690 A2 | 3/2006 |
| WO | 2006026690 A2 | 3/2006 |
| WO | 2006/043028 A1 | 4/2006 |
| WO | 2006/055114 A1 | 5/2006 |
| WO | 2006/055151 A1 | 5/2006 |
| WO | 2006/055152 A1 | 5/2006 |
| WO | 2006/086618 A1 | 8/2006 |
| WO | 2007/024865 | 3/2007 |
| WO | 2007/038202 A1 | 4/2007 |

(56) References Cited

FOREIGN PATENT DOCUMENTS

| | | |
|---|---|---|
| WO | 2007/045008 A1 | 4/2007 |
| WO | 2007/071429 | 6/2007 |
| WO | 2007/100849 A2 | 9/2007 |
| WO | 2007/135700 A2 | 11/2007 |
| WO | 2008/081489 A1 | 7/2008 |
| WO | 2008/085546 A2 | 7/2008 |
| WO | 2008/145175 A1 | 12/2008 |
| WO | 2009/003057 A1 | 12/2008 |
| WO | 2009/003691 A1 | 1/2009 |
| WO | 2009/014798 A1 | 1/2009 |
| WO | 2009/032823 A1 | 3/2009 |
| WO | 2009/078043 A1 | 6/2009 |
| WO | 2009/091785 A1 | 7/2009 |
| WO | 2009/146359 A1 | 12/2009 |
| WO | 2010/023370 A1 | 3/2010 |
| WO | 2010/031126 A1 | 3/2010 |
| WO | 2010/043966 A2 | 4/2010 |
| WO | 2010/075397 A2 | 7/2010 |
| WO | 2010/080201 A1 | 7/2010 |
| WO | 2011/038458 A1 | 4/2011 |
| WO | 2011/133207 A2 | 10/2011 |
| WO | 2012/024728 A1 | 3/2012 |
| WO | 2012/089963 A1 | 7/2012 |
| WO | 2012/097762 A1 | 7/2012 |
| WO | 2012/110514 A1 | 8/2012 |
| WO | 2012/146883 A1 | 11/2012 |
| WO | 2013/026092 A1 | 2/2013 |
| WO | 2013/053082 A1 | 4/2013 |
| WO | 2013/075166 A1 | 5/2013 |
| WO | 2013/117926 A1 | 8/2013 |
| WO | 2013/169467 A1 | 11/2013 |
| WO | 2014/015382 A1 | 1/2014 |
| WO | 2014/091293 A1 | 6/2014 |
| WO | 2014/092989 A1 | 6/2014 |
| WO | 2014/105475 A1 | 7/2014 |
| WO | 2014/110626 A1 | 7/2014 |
| WO | 2014/165906 A1 | 10/2014 |
| WO | 2014160149 A2 | 10/2014 |
| WO | 2014/197022 A2 | 12/2014 |
| WO | 2015/010170 A1 | 1/2015 |
| WO | 2015/031141 A2 | 3/2015 |
| WO | 2015/036652 A1 | 3/2015 |
| WO | 2015195495 A1 | 12/2015 |

OTHER PUBLICATIONS

Communication pursuant to Rule 94(3) EPC issued for EP 15 7 2 8 713.7 dated Jul. 11, 2018, 5 pages.
Communication under Rule 71(3) EPC for European Patent Application No. 15 731 219.0-1122, dated Jan. 14, 2021, 5 pages.

* cited by examiner

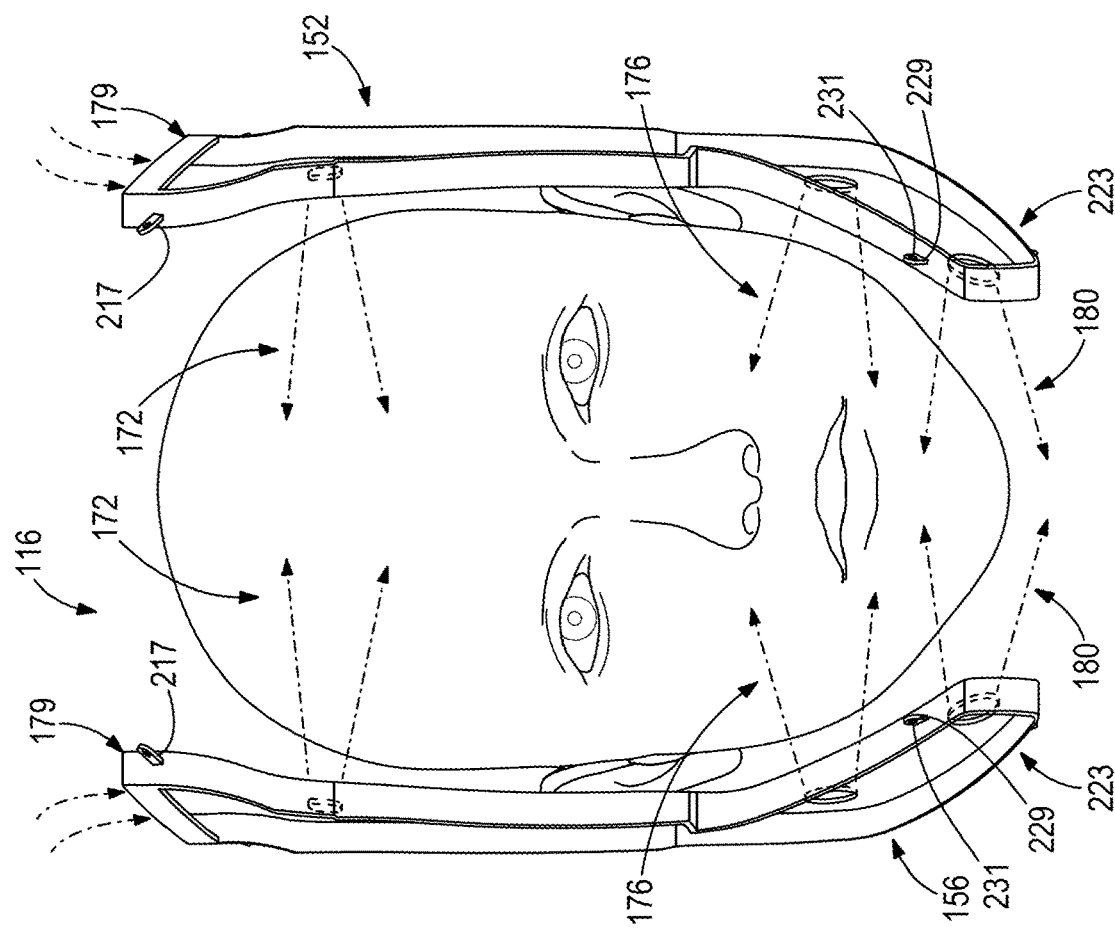
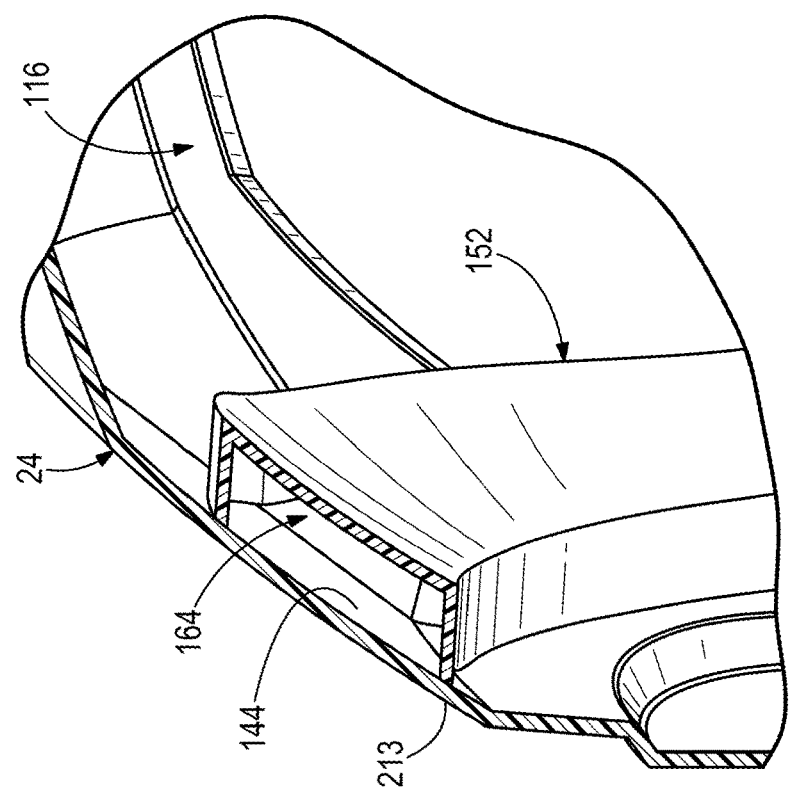

PROTECTIVE HEADWEAR WITH AIRFLOW

FIELD OF THE INVENTION

The present disclosure generally relates to protective headwear and, more particularly, to protective headwear with airflow.

BACKGROUND

Protective headwear such as, for example, welding helmets may be used in environments requiring respirators or other manners of introducing air into an interior of the protective headwear such as, for example, a powered air purifying respirator (PAPR) or a supplied air respirator (SAR). Some of these conventional welding helmets include a blower unit that delivers air to a manifold, which distributes air to an interior space of the welding helmet. Such conventional welding helmets lack comfort because they are heavy and distribute air to undesirable locations within the welding helmet. Some conventional welding helmets include a manifold or hose that extends over a wearer's head and distributes the air downward over a front of the wearer's face and into the wearer's eyes. Such a manifold or hose is heavy in construction and positions a lot of weight above and in front of a wearer's head and face to provide a center of gravity above and in front of a wearer's head and face. A center of gravity in this position applies significant torque and stress on a wearer's head, neck and body.

While the primary purpose of protective headwear with airflow is to provide respiratory protection, it also serves to protect users from heat stress. The poor design of the airflow delivery system does not maximize its potential for assisting in the body's thermoregulation to minimize heat stress. Additionally, the poor design of protective headwear with airflow leads to inefficient use of the airflow to maximize the user's thermal comfort and perception of air circulation which play a key role in defining user comfort. The comfort of protective headwear with airflow may have an impact on productivity and quality of the welder. Additionally, the air of conventional protective headwear is blown directly over and/or into the wearer's eyes, thereby drying the wearer's eyes or otherwise making the wearer uncomfortable.

Moreover, protective headwear typically has a majority of its weight on a front half of the headwear. This forward weight is often caused by the weight of an auto-darkening lens or other protective component(s) disposed on a front of the helmet. Positioning a majority of the weight on a front half of the protective headwear applies significant torque and stress on a wearer's head, neck and body.

SUMMARY

It is therefore desirable to have protective headwear that has an appropriate weight and location of a center of gravity, and provides airflow to an appropriate location within an interior of the protective headwear to effectively cool.

In one aspect, a protective headwear for providing airflow to an interior thereof is provided.

In one aspect, a protective headwear is provided and includes an airflow device for providing airflow to an interior of the protective headwear.

In one aspect, a protective headwear is provided and includes an outer shell including a first helmet duct and a second helmet duct spaced apart from the first helmet duct. Each of the first and second helmet ducts includes an exhaust port. The protective headwear also includes an airflow device in fluid communication with the outer shell. The airflow device includes an air source for providing an airflow and a coupling member coupled to the outer shell. The coupling member includes a first duct coupled to and in fluid communication with the first helmet duct to provide a first portion of the airflow to the first helmet duct, and a second duct coupled to and in fluid communication with the second helmet duct to provide a second portion of the airflow to the second helmet duct. The protective headwear may be a welding helmet.

In one aspect, a protective headwear is provided and includes an outer shell, a first shell duct coupled to the outer shell and including a first exhaust port, and a second shell duct coupled to the outer shell and spaced apart from the first shell duct. The second shell duct includes a second exhaust port. The protective headwear also includes a manifold positioned externally of the outer shell and configured to divert airflow into at least a first portion of airflow and a second portion of airflow. The manifold includes a first diversion member coupled to and in fluid communication with the first shell duct to provide the first portion of airflow to the first shell duct, and a second diversion member coupled to and in fluid communication with the second shell duct to provide the second portion of airflow to the second shell duct.

In one aspect, the first exhaust port of the first shell duct may be one of a plurality of exhaust ports, and the second exhaust port of the second shell duct may be one of a plurality of exhaust ports.

In one aspect, at least one of the plurality of exhaust ports of the first shell duct may be adjustable to adjust at least one of airflow direction and airflow volume exhaustible from the at least one of the plurality of exhaust ports of the first shell duct, and at least one of the plurality of exhaust ports of the second shell duct may be adjustable to adjust at least one of airflow direction and airflow volume exhaustible from the at least one of the plurality of exhaust ports of the second shell duct.

In one aspect, the at least one of the plurality of exhaust ports of the first shell duct that is adjustable may be rotatable to adjust air flow direction and may include a damper for adjusting airflow volume exhaustible there from, and the at least one of the plurality of exhaust ports of the second shell duct that is adjustable may be rotatable to adjust air flow direction and may include a damper for adjusting airflow volume exhaustible there from.

In one aspect, at least two of the plurality of exhaust ports of the first shell duct may be adjustable to adjust at least one of airflow direction and airflow volume exhaustible there from, and at least two of the plurality of exhaust ports of the second shell duct may be adjustable to adjust at least one of airflow direction and airflow volume exhaustible there from.

In one aspect, one of the plurality of exhaust ports of the first shell duct may be configured to exhaust air onto a wearer's forehead and another of the plurality of exhaust ports of the first shell duct may be configured to exhaust air onto a wearer's chin, and one of the plurality of exhaust ports of the second shell duct may be configured to exhaust air onto a wearer's forehead and another of the plurality of exhaust ports of the second shell duct may be configured to exhaust air onto a wearer's chin.

In one aspect, the protective headwear may be a welding helmet.

In one aspect, the protective headwear may further include a first flexible duct coupled to and between the first shell duct and the first diversion member to provide the first portion of airflow from the first diversion member to the first shell duct, and a second flexible duct coupled to and between the second shell duct and the second diversion member to provide the second portion of airflow from the second diversion member to the second shell duct.

In one aspect, the first shell duct may be offset to a first side of a plane extending through a center of the outer shell from a front to a rear of the outer shell, and the second shell duct may be offset to a second side of the plane.

In one aspect, a protective headwear is provided and includes an outer shell including an interior surface. The interior surface has a first side, a second side opposite the first side, a front between the first and second sides, and a top between the first and second sides. The protective headwear also includes a duct at least partially coupled to and extending along the first side of the interior surface of the outer shell. The duct includes an inlet through which air is configured to be introduced into the duct and an exhaust port through which air is configured to be exhausted from the duct and into an interior of the outer shell. The exhaust port may be positioned along the first side of the interior surface.

In one aspect, the exhaust port may be positioned in a bottom half of the outer shell.

In one aspect, the exhaust port may be adjustable to adjust at least one of airflow direction and airflow volume exhaustible there from.

In one aspect, the duct is a first duct, the inlet is a first inlet and the exhaust port is a first exhaust port. The protective headwear may further include a second duct at least partially coupled to and extending along the second side of the interior surface of the outer shell. The second duct may include a second inlet through which air is configured to be introduced into the second duct and a second exhaust port through which air is configured to be exhausted from the second duct and into the interior of the outer shell. The second exhaust port may be positioned along the second side of the interior surface.

In one aspect, at least a portion of air exhaustible from the exhaust port may be configured to be exhausted from the exhaust port substantially perpendicular to the first side of the interior surface.

In one aspect, at least a portion of air exhaustible from the exhaust port may be configured to be exhausted from the exhaust port away from the first side of the interior surface and toward the second side of the interior surface.

In one aspect, a protective headwear is provided and includes a headgear configured to engage a wearer's head and at least partially support the protective headwear on a wearer's head. The headgear includes a front, a rear opposite the front, a right side, and a left side opposite the right side. The protective headwear also includes an outer shell coupled to the headgear and including a shield positioned to the front of the headgear, and a duct at least partially coupled to and at least partially positioned in an interior of the outer shell. The protective headwear further includes a manifold positioned to the rear of the headgear and configured to divert airflow into at least a first portion of airflow and a second portion of airflow.

In one aspect, the manifold may include a first diversion member configured to divert the first portion of airflow and a second diversion member configured to divert the second portion of airflow. One of the first and second diversion members may be in fluid communication with the duct and may provide one of the first and second portions of airflow to the duct.

In one aspect, the protective headwear may further include a flexible duct coupled to and between the duct and the manifold to provide one of the first and second portions of airflow from the manifold to the duct.

In one aspect, the duct may be a first duct coupled to a first side of an interior surface of the outer shell and may at least partially extend along the first side. The protective headwear may further include a second duct coupled to a second side of the interior surface of the outer shell and may at least partially extend along the second side. The second side may be opposite the first side. The manifold may be coupled to and in fluid communication with both the first and second ducts to provide the first portion of airflow to the first duct and the second portion of airflow to the second duct.

In one aspect, the duct may be offset from a plane extending through a center of the headgear from the front to the rear of the headgear to one of the right or left sides of the headgear.

In one aspect, a protective headwear is provided and includes a headgear configured to engage a wearer's head and at least partially support the protective headwear on a wearer's head. The headgear includes a front, a rear opposite the front, a right side, and a left side opposite the right side. The protective headwear also includes an outer shell coupled to the headgear at a coupling location and including a shield positioned to the front of the headgear and a duct at least partially coupled to and at least partially positioned in an interior of the outer shell. The duct is located below the coupling location. The protective headwear further includes a manifold positioned to the rear of the headgear and configured to divert airflow into at least a first portion of airflow and a second portion of airflow.

In one aspect, the manifold may include a first diversion member configured to divert the first portion of airflow and a second diversion member configured to divert the second portion of airflow. One of the first and second diversion members may be in fluid communication with the duct to provide one of the first and second portions of airflow to the duct.

In one aspect, the duct may be comprised of a shell portion coupled to an interior surface of the outer shell and a flexible portion coupled to and between the shell portion and the manifold to provide one of the first and second portions of airflow from the manifold to the shell portion of the duct.

In one aspect, the shell portion and the flexible portion may be positioned completely below the coupling location.

In one aspect, the flexible portion of the duct may be substantially circular in a plane perpendicular to a longitudinal extent of the flexible portion.

In one aspect, the duct may be a first duct coupled to a first side of an interior surface of the outer shell and at least partially extending along the first side, and wherein the protective headwear may further include a second duct coupled to a second side of the interior surface of the outer shell below the coupling location and at least partially extending along the second side. The second side may be opposite the first side. The manifold may be coupled to and in fluid communication with both the first and second ducts to provide the first portion of airflow to the first duct and the second portion of airflow to the second duct.

In one aspect, the first duct may be comprised of a second shell portion coupled to the interior surface of the outer shell and a second flexible portion coupled to and between the second shell portion and the manifold to provide the first portion of airflow from the manifold to the first shell portion of the duct. The second duct may be comprised of a second shell portion coupled to the interior surface of the outer shell and a second flexible portion coupled to and between the second shell portion and the manifold to provide the second portion of airflow from the manifold to the second shell portion of the duct.

In one aspect, the first shell portion, the first flexible portion, the second shell portion and the second flexible portion may all be positioned completely below the coupling location.

In one aspect, the first and second flexible portions of the duct may be substantially circular in respective planes perpendicular to respective longitudinal extents of the first and second flexible portions.

In one aspect, the duct may include a plurality of exhaust ports configured to exhaust airflow onto locations of a wearer's face having highest concentrations of blood vessels.

In one aspect, at least one of direction and velocity of airflow exhausted from the plurality of exhaust ports may be adjustable.

In one aspect, a protective headwear is provided and includes a headgear configured to engage a wearer's head and at least partially support the protective headwear on a wearer's head. The headgear includes a front, a rear opposite the front, a right side, and a left side opposite the right side. The protective headwear also includes an outer shell coupled to the headgear at a coupling location and includes a shield positioned to the front of the headgear. The protective headwear also includes an airflow device including a duct at least partially coupled to and at least partially positioned in an interior of the outer shell and a coupling member coupled to and between the headgear and the airflow device.

In one aspect, the airflow device may further include a manifold in fluid communication with the duct and positioned to the rear of the headgear. The manifold may be configured to divert airflow into at least a first portion of airflow and a second portion of airflow, and the coupling member may be coupled to and between the headgear and the manifold.

In one aspect, the headgear may further include an adjustable member configured to adjust a size of the headgear. The coupling member may be coupled to and between the adjustable member and the manifold.

In one aspect, the coupling member may include a first closed loop wrapped around the manifold and a second closed loop wrapped around the adjustable member.

In one aspect, the coupling member may be an elastic coupling member.

In one aspect, a protective headwear is provided and includes an outer shell including an interior surface, a first shell duct coupled to the interior surface of the outer shell and including a first exhaust port and a second shell duct coupled to the interior surface of the outer shell and spaced-apart from the first shell duct. The second shell duct includes a second exhaust port. The protective headwear also includes a manifold positioned externally of the outer shell and including a first diversion member and a second diversion member. The first and second diversion members are configured to divert airflow into at least a first portion of airflow and a second portion of airflow. The protective headwear further including a first flexible duct and a second flexible duct. The first flexible duct is coupled to and between the first shell duct and the first diversion member to provide the first portion of airflow from the first diversion member to the first shell duct. The first flexible duct is substantially circular along a plane perpendicular to a longitudinal extent of the first flexible duct. The second flexible duct is coupled to and between the second shell duct and the second diversion member to provide the second portion of airflow from the second diversion member to the second shell duct. The second flexible duct is substantially circular along a plane perpendicular to a longitudinal extent of the second flexible duct.

In one aspect, the first flexible portion may be substantially circular along an entire length thereof, and the second flexible portion may be substantially circular along an entire length thereof.

In one aspect, the first shell duct may have a first portion that is substantially circular and a second portion that is non-circular. The first flexible portion may be coupled to the first portion of the first shell duct, and the second portion of the first shell duct may extend along the interior surface of the outer shell and may define a first exhaust port through which the first portion of airflow exhausts. The second shell duct may have a first portion that is substantially circular and a second portion that is non-circular. The second flexible portion may be coupled to the first portion of the second shell duct, and the second portion of the second shell duct may extend along the interior surface of the outer shell and may define a second exhaust port through which the second portion of airflow exhausts.

In one aspect, the first exhaust port may be one of a plurality of exhaust ports defined in the second portion of the first shell duct, and the second exhaust port may be one of a plurality of exhaust ports defined in the second portion of the second shell duct.

In one aspect, a protective headwear is provided and includes an outer shell and a duct. The outer shell includes an interior surface, and the interior surface has a first side, a second side opposite the first side, a front between the first and second sides, and a top between the first and second sides. The duct is at least partially coupled to and extends along the first side of the interior surface of the outer shell. The duct includes an inlet through which air is configured to be introduced into the duct and an exhaust port through which air is configured to be exhausted from the duct and into an interior of the outer shell. The exhaust port is positioned along the first side of the interior surface, and the exhaust port is adjustable between a plurality of positively secured positions to exhaust air therefrom in a plurality of directions.

In one aspect, the exhaust port may comprise an aperture defined in the duct and a baffle positioned in the aperture. The baffle may be movable within the aperture relative to the duct.

In one aspect, the baffle may be rotatable within the aperture relative to the duct.

In one aspect, the duct may include a first securement feature and the baffle may include a second securement feature. The first and second securement features may be engageable with each other to positively secure the baffle relative to the duct.

In one aspect, the first securement feature may be positioned adjacent the aperture defined in the duct and the second securement feature may be positioned on a perimeter of the baffle.

In one aspect, the first securement feature may be a projection and the second securement feature may be a plurality of recesses defined in the baffle. The projection may be selectively positioned in one of the plurality of recesses at a time.

In one aspect, the plurality of recesses may be defined in a perimeter of the baffle.

In one aspect, the first securement feature may include a plurality of projections.

In one aspect, the plurality of projections may be selectively positioned in a plurality of the plurality of recesses at a time.

In one aspect, the interior surface of the outer shell and the duct may together define an airflow path including four sides. The interior surface of the outer shell may define one of the four sides of the airflow path and the duct may define three of the four sides of the airflow path, and the aperture may be defined in a side of the duct that is opposite the interior surface of the outer shell.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

FIG. 7 is a cross-sectional view taken along line 7-7 in FIG. 1, according to one aspect of the present disclosure.

FIG. 8 is a front view of a portion of the airflow device shown in FIG. 1 with one example of an environment with which the airflow device may be associated, this view shows the airflow device directing airflow on a wearer's face without directing the airflow into the wearer's eyes, according to one aspect of the present disclosure.

DETAILED DESCRIPTION

Figure 1:
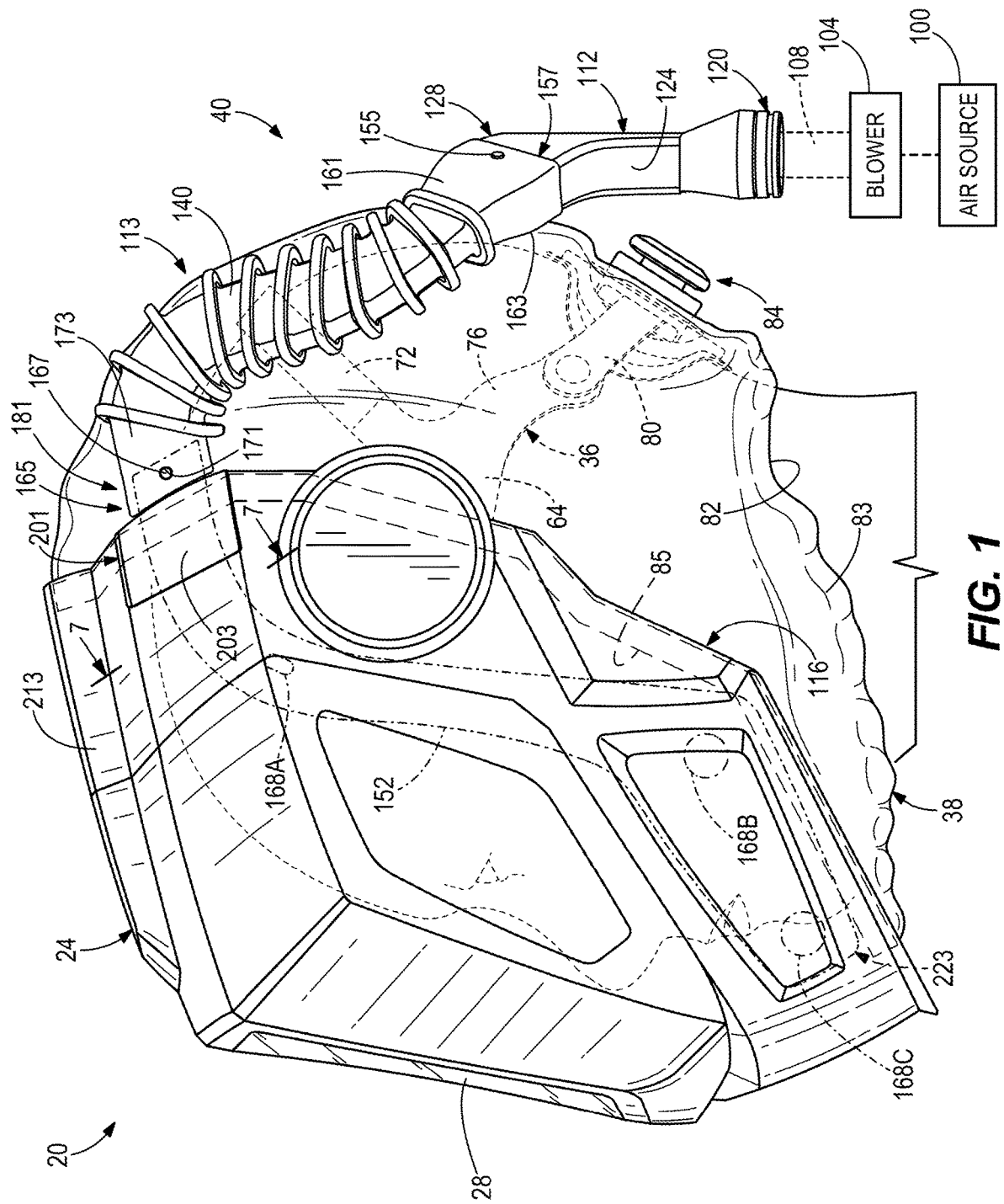
FIG. 1 is a side view of one example of protective headwear including one example of an airflow device for delivering air to an interior of the protective headwear, according to one aspect of the present disclosure.

Referring to FIGS. 1-7, one example of protective headwear 20 is illustrated. In this illustrated example, the protective headwear 20 is a welding helmet. In other examples, the protective headwear may be other types of protective headwear including, but not limited to, hard hats, bicycle helmets, military helmets, grinding shields, or any other type of headwear capable of providing protection to a wearer's head.

Returning to the illustrated example, the protective headwear 20 includes an outer shell 24, a first shield 28, a second shield 32 (beneath the first shield 28—see FIGS. 3 and 6), headgear 36 within the outer shell 24 to support the protective headwear 20 on a wearer's head, a head sleeve 38 coupled to the outer shell 24 and configured to at least partially surround a wearer's head, and an airflow device 40. The first shield 28 may be a welding shield and is coupled to the outer shell 24 over the second shield 32. The first shield 28 is darkened or capable of darkening in order to inhibit damage to a wearer's eyes while performing a welding process. In one example, the first shield 28 is an auto-darkening welding shield. The second shield 32 is coupled to the outer shell 24 beneath the first shield 28 and is darkened less than the first shield 28. In one example, the second shield 32 has no tinting or darkening and is completely transparent. In one example, the second shield 32 is a clear polycarbonate lens or shield. The second shield 32 may be referred to as a grinding shield.

With particular reference to FIG. 1, the exemplary headgear 36 is illustrated. Only a portion of and only one side of the headgear 36 is illustrated in FIG. 1, but it should be understood that the headgear 36 is a substantial mirror image about a vertical plane extending through a center of the headgear 36 (and a wearer's head when the headgear is worn) from a front of the protective headwear 20 to a rear of the protective headwear 20. In other words, the headgear 36 is symmetrical on both sides of a wearer's head. The headgear 36 is capable of engaging a wearer's head and supporting the protective headwear 20 on the wearer's head. The headgear 36 may be coupled to the outer shell 24 of the protective headwear 20 in a variety of manners such as, for example, movably coupled, rigidly coupled, unitarily formed with, among other manners.

In the illustrated example, the headgear 36 includes a side plate 64 on each side of the headgear 36, a forehead strap (not shown), a top strap 72, a rear strap 76, an occipital strap 80 and an adjustable member 84 coupled to the occipital strap 80. In one example, the top strap 72 may be pivotally coupled at its ends to respective side plates 64 and may be positioned to extend over a crown or top of a wearer's head. In another example, the top strap 72 may be rigidly or unitarily formed as one-piece with the side plates 64. In one example, the rear strap 76 may be pivotally coupled at its ends to respective side plates 64 and is positioned to extend around a rear of a wearer's head. In another example, the rear strap 76 may be rigidly or unitarily formed as one-piece with side plates 64.

In one example, the occipital strap 80 may be pivotally connected at its ends to the side plates 64, may extend under the side plates 64 (i.e., between the side plates and a wearer's head), may drop down below the rear strap 76, and may wrap around or extend along the occipital crest of a wearer's head, then may extend under the occipital crest. In another example, the occipital strap 80 may be pivotally connected at its ends to the side plates 64, may be positioned externally of the side plates 64 (i.e., the side plates 64 are between ends of the occipital strap 80 and a wearer's head), may drop down below the rear strap 76, and may wrap around or extend along the occipital crest of a wearer's head, then may extend under the occipital crest.

The occipital strap 80 may assist with applying pressure, originating from the protective headwear 20, to be applied to bony structure (e.g., the occipital bone and crest of a skull) of the wearer's head where the wearer has less of a perception of pressure than on soft tissue of the wearer's head.

The illustrated example of the headgear 36 is provided to demonstrate principles of the present disclosure and is not intended to be limiting upon the present disclosure. Rather, the protective headwear 20 may include any type of headgear and all such possibilities are intended to be with in the spirit and scope of the present disclosure.

With continued reference to FIG. 1, the head sleeve 38 is coupled to an interior surface 144 of the outer shell 24 and defines an opening 82 in a bottom thereof to allow a wearer's head to insert into and withdraw from an interior of the head sleeve 38 and an interior 116 of the protective headwear 20. In the illustrated example, the head sleeve 38 includes elastic or other resilient member 83 around the opening 82 to facilitate cinching or compression of the head sleeve 38 around a wearer's neck, thereby closing-off, eliminating or at least reducing the likelihood of air entering into or escaping from the interior 116 of the protective headwear defined by the head sleeve 38 and the outer shell 24. In another example, the head sleeve 38 may include a drawstring around the opening 82 to selectively open and cinch or close the opening 82.

The head sleeve 38 may be coupled to the outer shell 24 in a variety of manners. In one example, the head sleeve 38 is coupled to the interior surface 144 of the outer shell 24 with coupling member 85. In the illustrated example, the coupling member is a hook-and-loop type fastener 85 (see FIG. 1). Alternatively, the head sleeve 38 may be coupled to the interior surface 144 of the outer shell 24 in a variety of other manners including, but not limited to, snaps, screws, detents, buttons, adhesive, bonding, welding, or any other type of permanent, semi-permanent or removable manner, with all of such possibilities intended to be within the spirit and scope of the present disclosure.

The head sleeve 38 cooperates with the outer shell 24 to provide protection to a wearer's head and neck, along with providing an at least partially controlled environment in which the wearer's head is positioned. The controlled environment within the outer shell 24 and head sleeve 38 is at least partially controllable with respect to airflow within the protective headwear 20. The airflow device 40 provides an airflow to the interior 116 of the protective headwear 20 to provide fresh, breathable air for the wearer while also controlling the temperature or at least the perception of temperature on a wearer's head due to convection. The head sleeve 38, outer shell 24, the controlled environment created therein, and the airflow device 40 provide a more comfortable environment within the protective headwear 20 when the protective headwear 20 may be worn in an uncomfortable environment.

Figure 2:
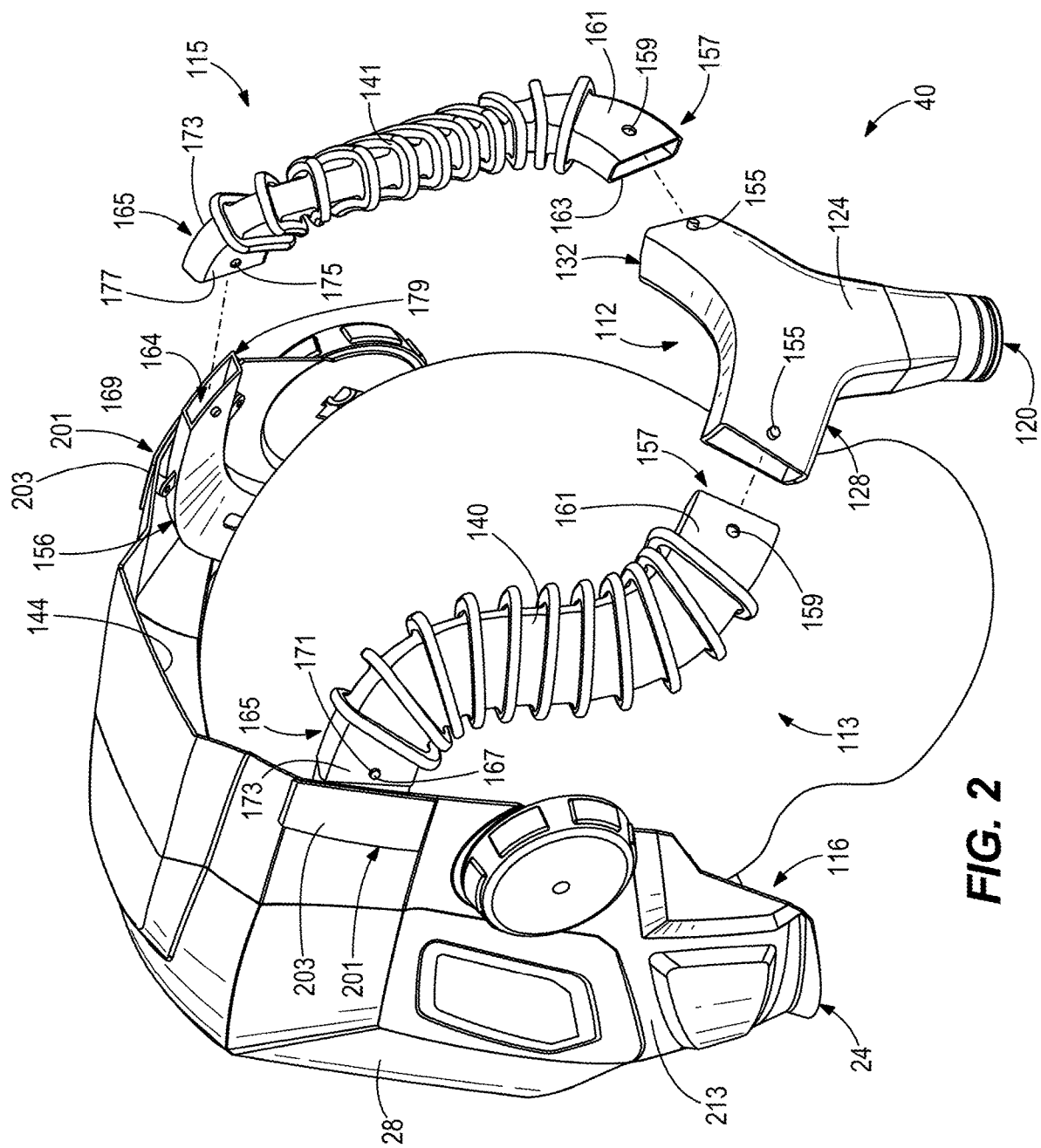
FIG. 2 is a rear, partially exploded perspective view of a portion of the protective headwear and the airflow device shown in FIG. 1, in this view a head sleeve of the protective headwear is removed to facilitate viewing of the interior of the protective headwear, according to one aspect of the present disclosure.
Figure 3:
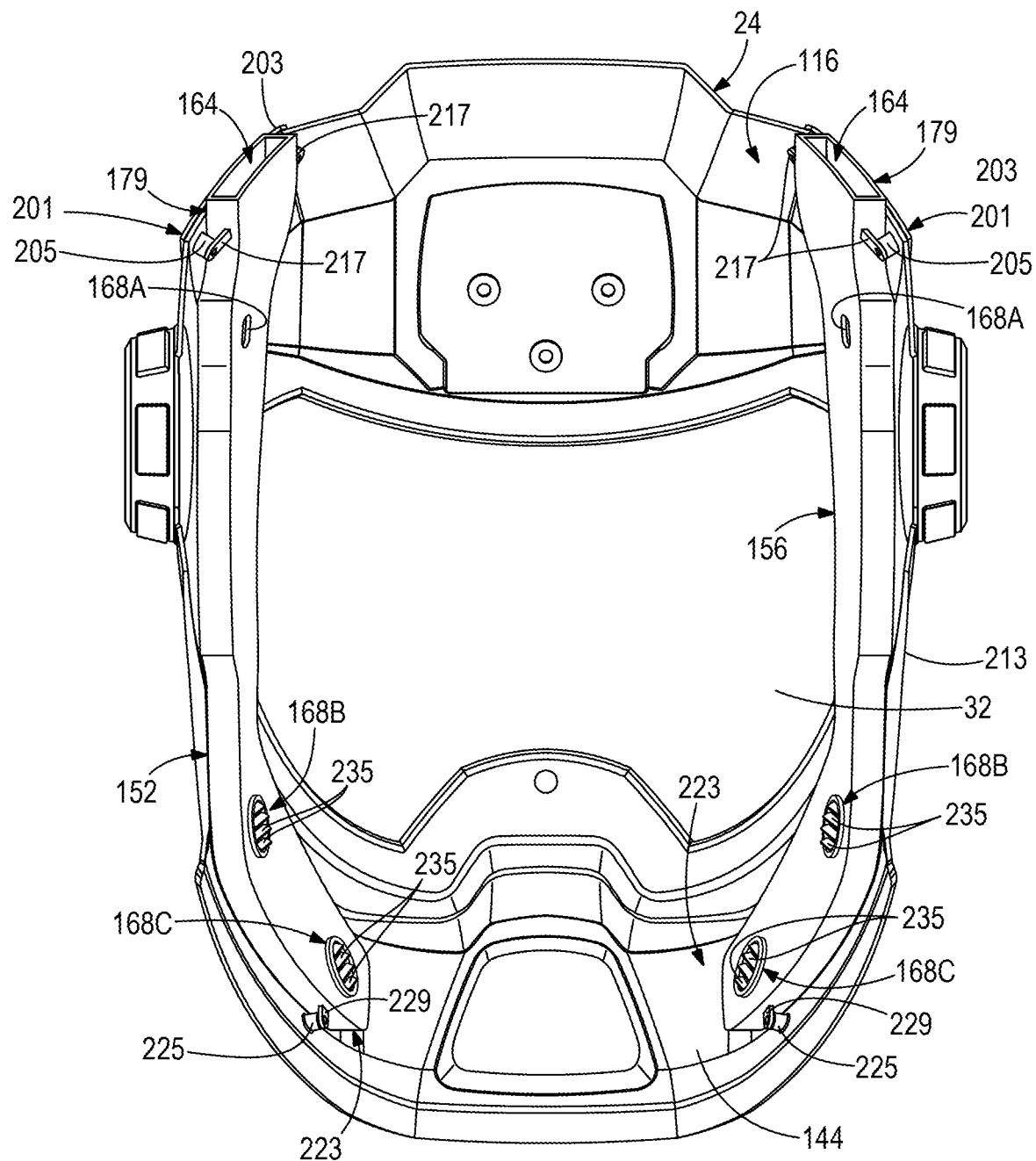
FIG. 3 is a rear view of a portion of the protective headwear shown in FIG. 1, according to one aspect of the present disclosure.
Figure 4:
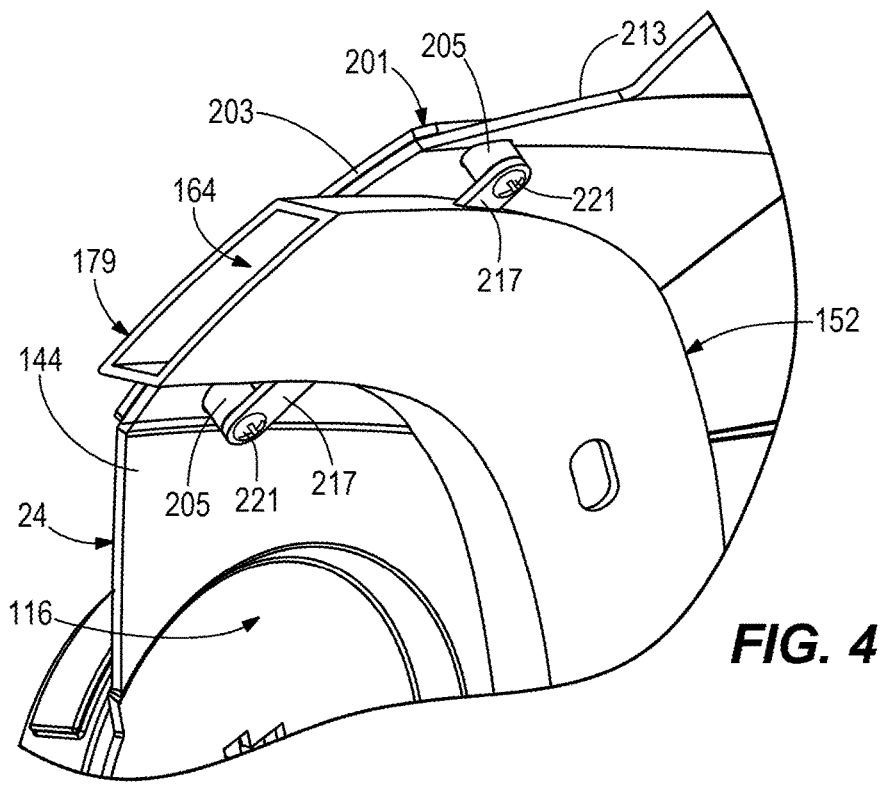
FIG. 4 is a rear perspective view of a portion of the protective headwear shown in FIG. 1, this view shows a portion of the airflow device coupled to a shell of the protective headwear, according to one aspect of the present disclosure.
Figure 5:
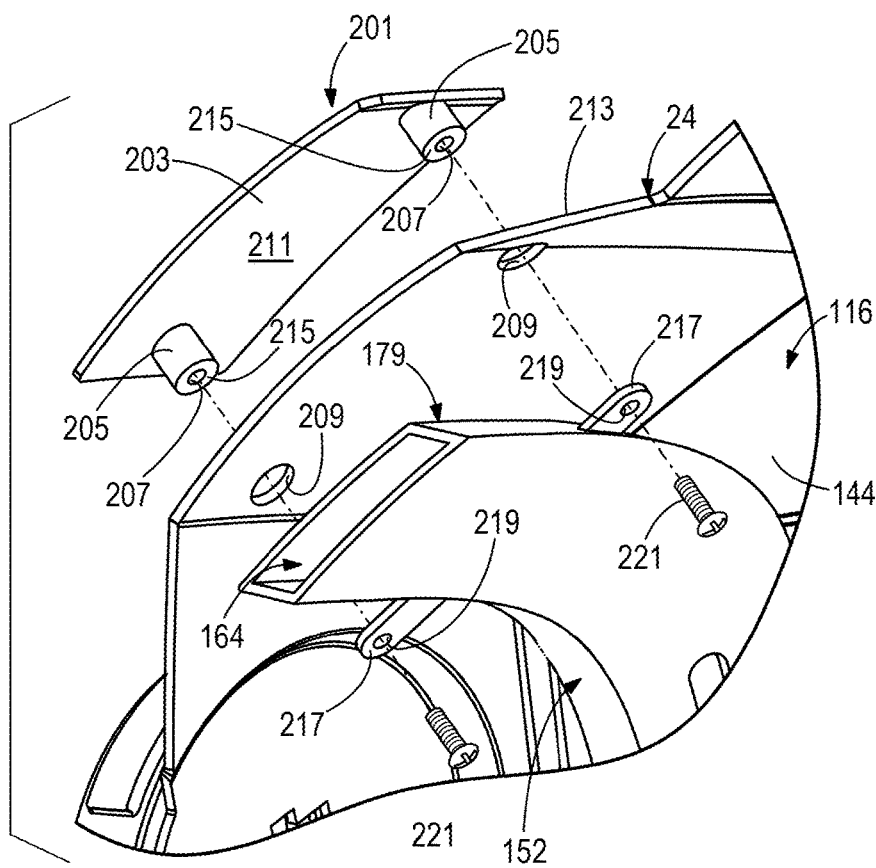
FIG. 5 is an exploded view of the portion of the protective headwear shown in FIG. 4, according to one aspect of the present disclosure.
Figure 6:
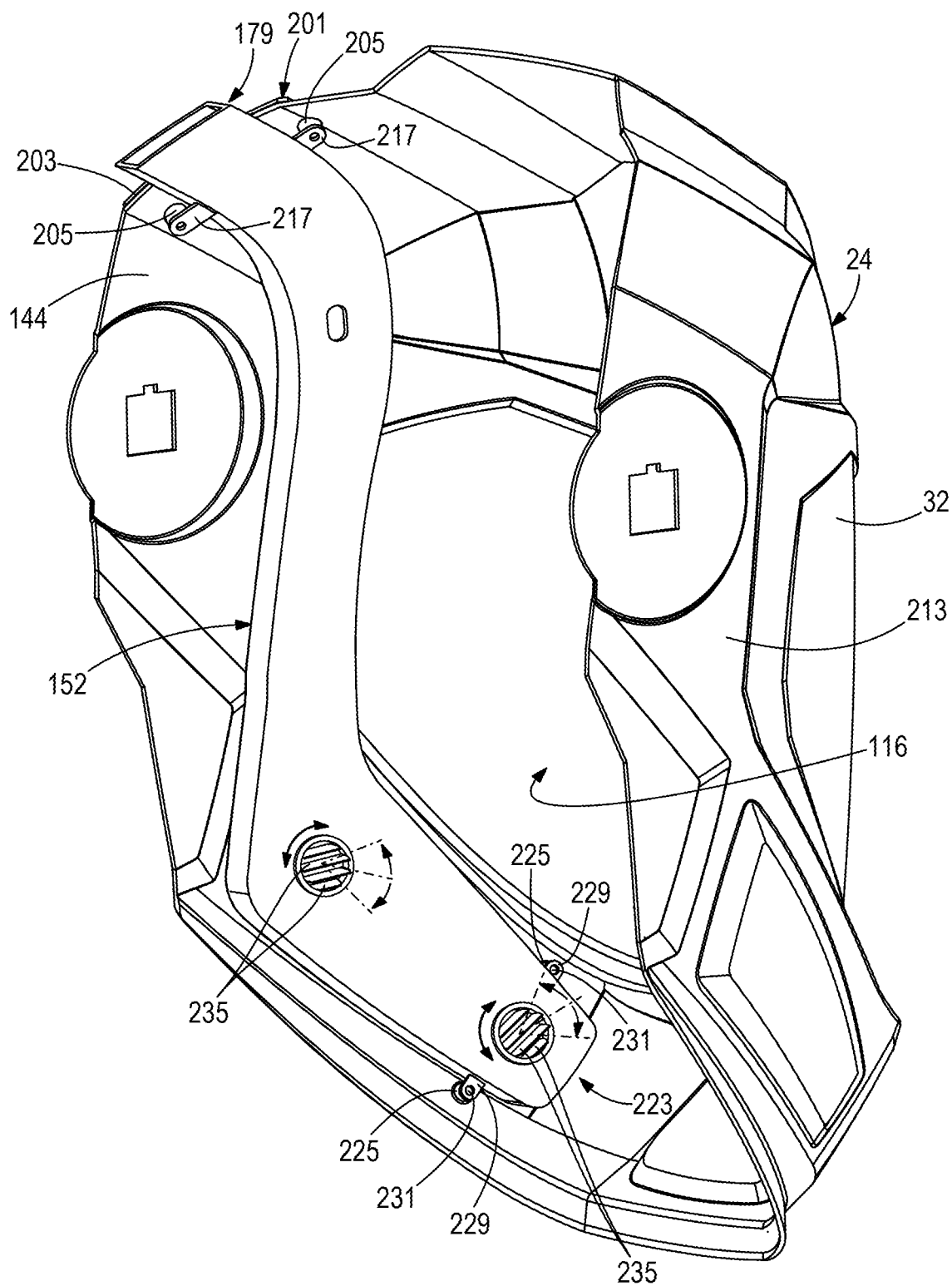
FIG. 6 is a rear perspective view of a portion of the protective headwear and airflow device shown in FIG. 1, in this view the head sleeve of the protective headwear is removed to expose the interior of the protective headwear and a plurality of air vents in the airflow device, according to one aspect of the present disclosure.

With continued reference to FIGS. 1 and 2, the airflow device 40 includes an air source 100, a blower 104, a hose 108 or other air communication device, a manifold or coupling member 112, and a pair of ducts or tubes 113, 115 extending from the coupling member 112 to a location within the interior 116 of the protective headwear 20. The blower 104 is in fluid communication with the air source 100 and blows air from the air source 100, through the hose 108, and into the coupling member 112, which is coupled to the protective headwear 20 to communicate air from the hose 108 to an interior space 116 within the outer shell 24 of the protective headwear 20. The airflow device 40 may also include one or more filters for filtering the air prior to communication of the air to the interior space 116 of the protective headwear 20.

The coupling member 112 includes an attachment member 120 at an end thereof for coupling the hose 108 to the coupling member 112. The coupling member 112 defines an internal cavity therein for receiving air from the hose 108 and diverting the air downstream to the interior 116 of the protective headwear 20. In the illustrated example, the coupling member 112 includes a "Y" shape comprising a receiving portion 124, a first diversion member 128 and a second diversion member 132 spaced-apart and extending away from the first diversion member 128. The first diversion member 128 and the second diversion member 132 divide the airflow into two streams or portions and communicate the air along two downstream paths into respective first and second ducts 113, 115 and ultimately into different portions of the interior space 116 of the protective headwear 20.

The first diversion member 128 is coupled to the first duct 113 and the second diversion member 132 is coupled to the second duct 115. The first duct 113 is positioned along a first side of a wearer's head and the second duct 115 is positioned along a second side of the wearer's head opposite the first side.

In the illustrated example, the first duct 113 includes a first flexible portion or duct 140 and a first shell portion or first helmet duct 152, and the second duct 115 includes a second flexible portion or duct 141 and a second shell portion or duct 156. The first and second flexible portions 140, 141 are respectively coupled to the first and second diversion members 128, 132. The first and second flexible portions 140, 141 may be coupled to the first and second diversion members 128, 132 in a variety of manners and all manners are intended to be within the spirit and scope of the present disclosure. In the illustrated example, each of the first and second diversion members 128, 132 includes a first protection 155 extending from a first or external side of the first and second diversion members 128, 132 and a second projection extending from a second or internal side of the first and second diversion members 128, 132 opposite the first side. Each of first ends 157 of the first and second flexible portions 140, 141 define a first aperture 159 in a first or external side 161 thereof and a second aperture in a second or interior side 163 thereof. The apertures 159 are complementary sized and shaped to the protections 155 to accommodate insertion of the projections 155 into the apertures 159, thereby coupling the first ends 157 of the first and second flexible portions 140, 141 to the manifold or coupling member 112. In other examples, each of the first and second diversion members 128, 132 may include only a single projection and the first ends 157 of the first and second flexible portions 140, 141 may include only a single aperture to couple the flexible portions 140, 141 to the manifold or coupling member 112. In further examples, the first and second flexible portions 140, 141 may include one or more projections and the coupling member may include one or more complementary apertures for coupling the first and second flexible portions 140, 141 to the coupling member 112. In still other examples, the first ends 157 of the flexible portions 140, 141 may be additionally coupled to the manifold or coupling member 112 with adhesive.

Second ends 165 of the first and second flexible portions 140, 141 are respectively coupled to the first and second shell portions 152, 156 in similar manners to the illustrated example of the manner in which the first ends 157 of the first and second flexible portions 140, 141 are coupled to the manifold or coupling member 112. In the illustrated example, each of the first and second shell portions 152, 156 includes a first protection 167 extending from a first or external side of the first and second shell portions 152, 156 and a second projection 169 extending from a second or internal side of the first and second shell members 152, 156 opposite the first side. Each of second ends 165 of the first and second flexible portions 140, 141 define a first aperture 171 in a first or external side 173 thereof and a second aperture 175 in a second or interior side 177 thereof. The apertures 171, 175 are complementary sized and shaped to the protections 167, 169 to accommodate insertion of the projections 167, 169 into the apertures 171, 175, thereby coupling the second ends 165 of the first and second flexible portions 140, 141 to the first and second shell portions 152, 156. In other examples, each of the first and second shell portions 152, 156 may include only a single projection and the second ends 165 of the first and second flexible portions 140, 141 may include only a single aperture to couple the flexible portions 140, 141 to the first and second shell portions 152, 156. In further examples, the first and second flexible portions 140, 141 may include one or more projections and the first and second shell portions 152, 156 may include one or more complementary apertures for coupling the first and second flexible portions 140, 141 to the first and second shell portions 152, 156. In still other examples, the second ends 165 of the flexible portions 140, 141 may be additionally coupled to the first and second shell portions 152, 156 with adhesive.

With reference to FIGS. 1-4, ends 179 of the first and second shell portions 152, 156 are positioned externally, outside, behind or beyond an outermost edge of the outer shell 24. Also, in the illustrated example, the first and second flexible portions 140, 141 are coupled to ends 179 of the first and second shell portions externally, outside, behind or beyond an outermost edge of the outer shell 24. In the illustrated example, the head sleeve 38 defines a pair of apertures or openings 181 through which the ends 179 of the first and second shell portions extend to facilitate the first and second ducts 113, 115 from passing from an exterior of the outer shell 24, through the head sleeve 38, and to the interior 116 of the protective headwear 20.

The flexible portions 140, 141 allow the first and second ducts 113, 115 to be adjusted to accommodate movement of the outer shell 24 relative to the headgear 36 between a downward operating position and an upward inoperative position, heads of different sizes and shapes, different types of headgear, or other reasons. In some examples, the first and second ducts 113, 115 may not include a flexible portion and, instead, the first and second ducts 113, 115 may be completely rigid and extend from the manifold or coupling member 112 to their termination location within the outer shell 24.

In the illustrated example, the airflow device 40 is not coupled to the headgear 36 and the coupling member 112 is positioned to a rear and rests at a rear of a wearer's head (see FIG. 1) either spaced-apart from the headgear 36 and the wearer's head or against at least one of the headgear 36 and a rear of the wearer's head. In another example, the airflow device 40 is coupled to the headgear 36 for additional support by the coupling member 112 being coupled to the headgear 36 at a rear of the headgear and rear of a wearer's head. In one example, an attachment member couples the coupling member 112 to the rear strap 76 of the headgear 36. The attachment member may be a strap or other type of attachment members. In other examples, the coupling member 112 may be coupled to the top strap 72, the occipital strap 80, or the side plate 64. In still other examples, the coupling member 112 may be coupled to any combination of the top strap 72, the rear strap 76, the occipital strap 80 and the side plate 64. In further examples, any portion(s) of the airflow device 40 may be coupled to any portion of the headgear 36. It should be understood that the airflow device 40 may or may not be coupled to any other portion of the protective headwear 20 and all of such possibilities are intended to be within the spirit and scope of the present disclosure.

Referring now to FIGS. 1-7, the first shell portion 152 is coupled to and in fluid communication with the first flexible portion 140 to receive air from the coupling member 112 and the second shell portion 156 is coupled to and in fluid communication with the second flexible portion 141 to receive air from the coupling member 112.

The first and second shell portions 152, 156 are similar in shape and configuration and it should be understood that the second shell portion 156 is a substantial mirror image of the first shell portion 152. In other words, in the illustrated example, the protective headwear 20 is symmetrical on both sides of a wearer's head. In another example, the protective headwear 20 may not be symmetrical on both sides and the first and second shell portions 152, 156 may not be substantially identical in shape and configuration. In a further example, the protective headwear 20 may include only one shell portion on only one side of the protective headwear 20. In such an example, the coupling member 112 may only include a single diversion member (or no diversion member because it may not be necessary to divert the air flow) coupled to and in fluid communication with the single shell portion. In still another example, the protective headwear 20 may include more than two shell portions. In such an example, the coupling member 112 may include a complementary number of diversion members to couple to and be in fluid communication with the plurality of shell portions included in the protective headwear 20. Additionally, in such an example, the first and second ducts 113, 115 may include a complimentary number of flexible portions to couple the manifold or coupling member 112 to the shell portions.

Returning to the illustrated example and to FIGS. 1-7, the first and second shell portions 152, 156 are coupled to the outer shell 24. The first and second shell portions 152, 156 may be coupled to the outer shell 24 in a variety of manners and all possibilities are intended to be within the spirit and scope of the present disclosure. For example, the first and second shell portions 152, 156 may be coupled to the outer shell by fastening, bonding, welding, unitarily forming as one-piece with, friction-fit, interference-fit, tongue and groove, detent, snap-fit, hook and loop type fastening, or any other manner of permanently, semi-permanently, or removably coupling.

In the illustrated example, the first and second shell portions 152, 156 are coupled to outer shell in similar manners and, therefore, only coupling of the first shell portion 152 will be described with it being understood that the description may apply mutatis mutandis to coupling the second shell portion 156 to the outer shell 24. In other examples, the first and second shell portions 15, 156 may be coupled to the outer shell 24 in different manners.

With reference to FIGS. 1-7, the protective headwear 20 includes a coupling member 201 including a base 203 and a pair of projections 205 extending from the base 203. An aperture 207 is defined in each of the projections 205. The outer shell 24 defines a pair of apertures 209 defined therein configured to respectively receive the projections 205. With the projections 205 inserted into the apertures 209 and an interior surface 211 of the base 203 engaging an outer surface 213 of the outer shell 24, ends 215 of the projections 205 are positioned in the interior 116 of the outer shell 24. The first shell portion 152 includes a pair of flanges 217, each of which defines an aperture 219 therein. The flanges 217 engage ends 215 of the projections 205 and apertures 219 of the flanges 217 align with apertures 207 in the projections. Fasteners 221 are inserted (e.g., threaded in the illustrated example) into the aligned apertures 207, 219 to couple the first shell portion 152 to the outer shell 24. The first shell portion 152 is also coupled to the outer shell 24 near a second end 223 of the first shell portion 152. A pair of projections 225 extend from the interior surface 144 of the outer shell 24 and each projection 225 defines an aperture therein. The first shell portion 152 includes a pair of flanges 229, each of which defines an aperture 231 therein. The flanges 229 engage the projections 225 and apertures 231 of the flanges 229 align with apertures in the projections 225. Fasteners are inserted (e.g., threaded fasteners) into the aligned apertures to couple the first shell portion 152 to the outer shell 24 near the second end 223 of the first shell portion 152.

With particular reference to FIG. 7, an airflow path or duct cavity 164 is defined along each of two sides of the interior surface 144 of the outer shell 24 (right side and left side of interior surface of the outer shell) by a combination of the first and second shell portions 152, 156 and the interior surface 144 of the outer shell 24. Three sides of each duct cavity 164 is defined by the respective first or second shell portion 152, 156 and a fourth side of each duct cavity 164 is defined by the interior surface 144 of the outer shell 24.

Referring now to FIGS. 1, 3, 4, 6 and 8, each of the first and second shell portions 152, 156 includes a plurality of exhaust ports 168 configured to exhaust air from the first and second shell portions 152, 156 to the interior space 116 of the protective headwear 20. In the illustrated example, each helmet duct 152, 156 includes three exhaust ports 168A, 168B, 168C. Alternatively, the shell portions 152, 156 may include any quantity of exhaust ports and be within the spirit and scope of the present disclosure. In the illustrated example, exhaust port 168A has a different shape than exhaust ports 168B, 168C. In this illustrated example, exhaust port 168A is generally oval in shape and exhaust ports 168B, 168C are generally round in shape. It should be understood that the exhaust ports may have any shape, may be different in shape relative to each other in any combination, or and may all be similar in shape, and all of such possibilities are intended to be within the spirit and shape of the present disclosure. Returning to the illustrated example, exhaust ports 168B, 168C are independently adjustable to selectively alter a directional flow of the air exhausting from the exhaust ports 168B, 168C and exhaust port 168A is fixed and not adjustable. It should be understood that any number of the exhaust ports 168 may be adjustable, rigid and non-adjustable, and any combination thereof and all of such possibilities are intended to be within the spirit and scope of the present disclosure.

In one example, the adjustable exhaust ports 168 have adjustability along multiple axes. In another example, the adjustable exhaust ports 168 have adjustability along two axes. In a further example, the adjustable exhaust ports 168 have adjustability along three axes. The illustrated example provides adjustable exhaust ports 168B, 168C adjustable along three axes. The direction of the exhaust ports 168 may be adjusted to accommodate varying sizes and shapes of wearers' faces, variance in environments in which the protective headwear 20 may be used, and accommodate wearer's preferences with respect to where and how they desire airflow to impact their face.

Additionally, with respect to the illustrated example, the adjustable exhaust ports 168B, 168C include dampers 235 for adjusting a quantity of airflow passing there through. The dampers are adjustable to a variety of positions between and including a fully opened position, in which the dampers allow the most airflow to pass there through, and a fully closed position, in which the dampers prevent any airflow from passing there through. Any number of the exhaust ports 168 may include dampers (including zero and all of the ports) and all of such possibilities are intended to be within the spirit and scope of the present disclosure.

Figure 9:
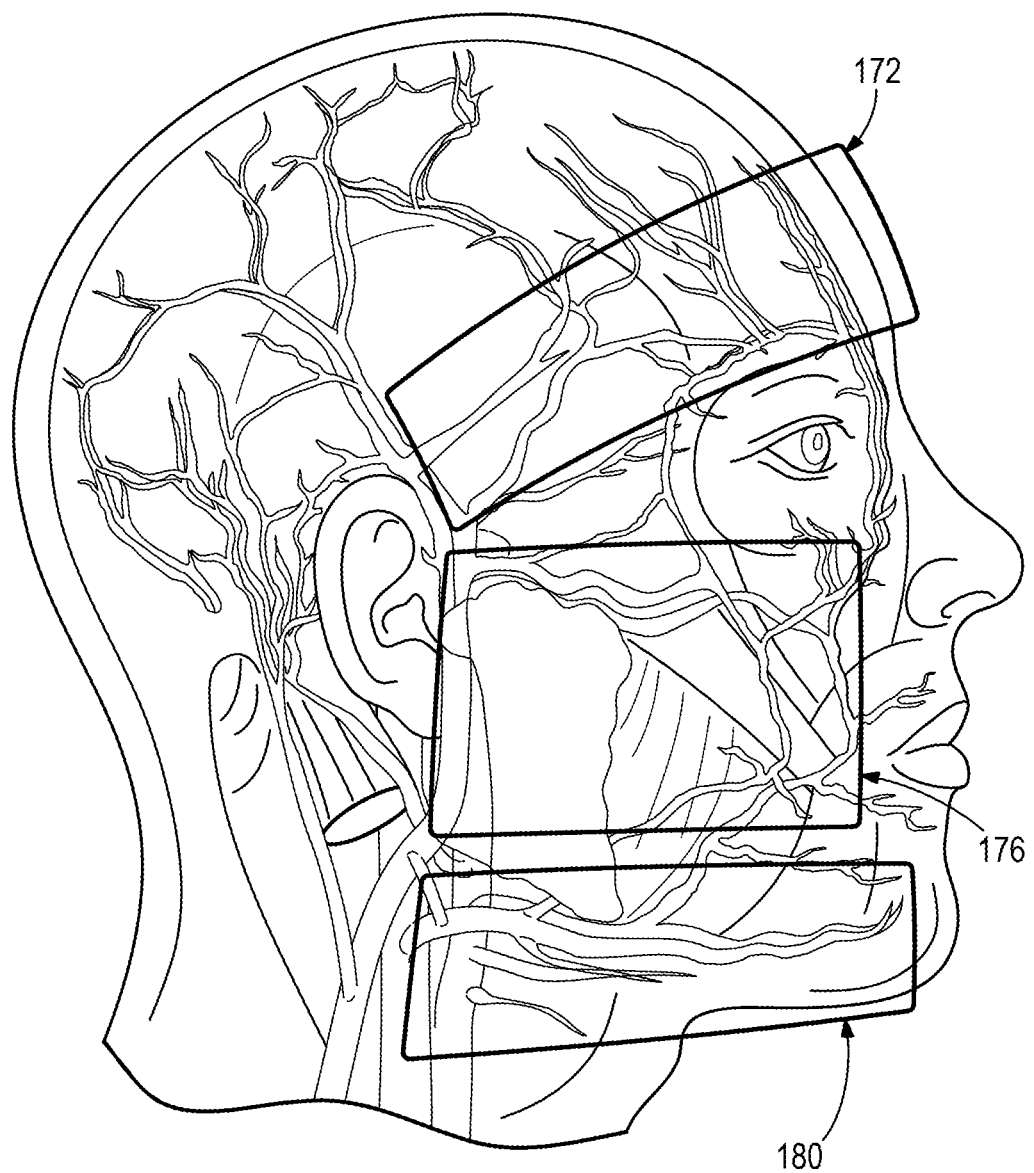
FIG. 9 is a diagram of another example of an environment with which the airflow device may be associated, according to one aspect of the present disclosure.

With continued reference to FIGS. 1, 3, 4, 6 and 8 and additional reference to FIG. 9, the exhaust ports 168 are positioned along the first and second shell portions 152, 156 to supply air to particular portions of the wearer's head. In the illustrated example, top exhaust ports 168A supply air to first zones 172 (one on each side of the wearer's head), middle exhaust ports 168B supply air to second zones 176 (one on each side of the wearer's head), and bottom exhaust ports 168C supply air to third zones 180 (one on each side of the wearer's head). In one example, the first zones 172 generally correspond to temples and/or a forehead of the wearer's head, second zones 176 generally correspond to cheeks of the wearer's head, and third zones 180 generally correspond to jaw and/or neck areas of the wearer's head. In other examples, the zones may correspond to other portions of a wearer's head.

In the illustrated example, the exhaust ports 168 may be positioned to exhaust air generally perpendicular to the portions or zones of the wearer's head associated with the exhaust ports 168. Exhausting air at an angle generally perpendicular to the associated portion of the wearer's head generates more turbulence (compared to a laminar exhaust stream when air is delivered parallel or generally parallel to a portion of the wearer's head) when the exhaust stream engages the portion of the wearer's head.

In one example, the zones or portions of the wearer's head may be determined based on those areas of a wearer's head that have a higher perception of airflow and cooling. For example, a human face has certain areas with large concentrations of superficial blood vessels such as temples, forehead, cheeks, jaw and neck. Additionally, it is important to avoid blowing air directly into a wearer's eyes in order to avoid drying a wearer's eyes or otherwise deteriorating a wearer's comfort level. Moreover, exhausting airflow in the manner performed by the present disclosure may blow air onto a larger percentage of the wearer's face than conventional airflow, which is blown from a location above the wearer's forehead straight down over the wearer's face and into the wearer's eyes.

In some examples, a velocity and/or an angle at which air exhausts from the exhaust ports 168 may be adjusted. For example, the position and/or exhaust apertures associated with the exhaust ports 168 or the exhaust ports 168 themselves may be adjusted to adjust the exhaust velocity and/or direction of the air (as described above), the coupling member 112 may include an actuator and/or damper that may be actuated to adjust the exhaust velocity and/or angle of the air, the blower 104 may be adjusted to adjust the exhaust velocity and/or angle of the air, or any of a wide variety of other manners of adjusting air velocity and/or air angle are possible, and all of such possibilities are intended to be within the spirit and scope of the present disclosure.

The components of the present disclosure utilized to communicate air to an interior space 116 of the protective headwear 20 are coupled and positioned relative to the protective headwear 20 to locate a center of gravity in a more ideal location relative to a wearer's head, thereby decreasing the level of stress and pressure applied to a wearer's head. For example, the manifold or coupling member 112 is positioned near or to a rear of the protective headwear 20 behind a wearer's head, thereby adding weight to a rear of the protective headwear behind a wearer's head and biasing the center of gravity in a rearward direction. Positioning weight behind a wearer's head via the manifold and portions of the first and second ducts 113, 115 offsets weight in front of the wearer's head provided by the outer shell 24 and shields 28, 32. During welding or other operating process, a wearer may be looking forward and downward, thereby shifting the center of gravity forward of a middle of the wearer's head. By locating the coupling member 112 at a rear of the protective headwear 20, the coupling member 112 and other air communication components contribute to positioning the center of gravity more towards a rear of the protective headwear 20 than it would otherwise be without the coupling member 112 and other air components being positioned where they are. Additionally, the first and second shell portions 152, 156 are minimal in size, weight and profile, and are appropriately positioned to contribute to a more ideal location of the center of gravity. In some examples, a more ideal location of the center of gravity of the protective headwear 20 is over a middle or mid-line of the wearer's head, thereby decreasing any unnecessary torque applied to a wearer's head and neck by having the center of gravity located toward a front or a rear of the protective headwear 20. Furthermore, extending one helmet duct along each side of the protective headwear 20 (compared to a single large duct over a top of a wearer's head) requires less material, thereby reducing the overall weight of the protective headwear 20. A net effect of the components associated with providing airflow to an interior 116 of the protective headwear 20 will be to position the center of gravity closer to a mid-line of the wearer's head.

Referring now to FIGS. 10-19, another example of protective headwear 20' is illustrated. The protective headwear 20' illustrated in FIGS. 10-19 is capable of including all the structure/components and having all of the functionality of the protective headwear 20 illustrated in FIGS. 1-9, and all of such similar structure/components included in the protective headwear 20' have the same reference number and an "'".

In this illustrated example, the protective headwear 20' is a welding helmet. In other examples, the protective headwear may be other types of protective headwear including, but not limited to, hard hats, bicycle helmets, military helmets, grinding shields, or any other type of headwear capable of providing protection to a wearer's head.

Returning to the illustrated example, the protective headwear 20' includes an outer shell 24', a first shield 28', a second shield 32' (see FIGS. 11 and 13), headgear 36' within the outer shell 24' to support the protective headwear 20' on a wearer's head, a head sleeve 38' coupled to the outer shell 24' and configured to at least partially surround a wearer's head, and an airflow device 40'. The first shield 28' may be a welding shield and is coupled to the outer shell 24' over the second shield. The first shield 28' is darkened or capable of darkening in order to inhibit damage to a wearer's eyes while performing a welding process. In one example, the first shield 28' is an auto-darkening welding shield. The second shield is coupled to the outer shell 24' beneath the first shield 28' and is darkened less than the first shield 28'. In one example, the second shield has no tinting or darkening and is completely transparent. In one example, the second shield is a clear polycarbonate lens or shield. The second shield may be referred to as a grinding shield.

Figure 10:
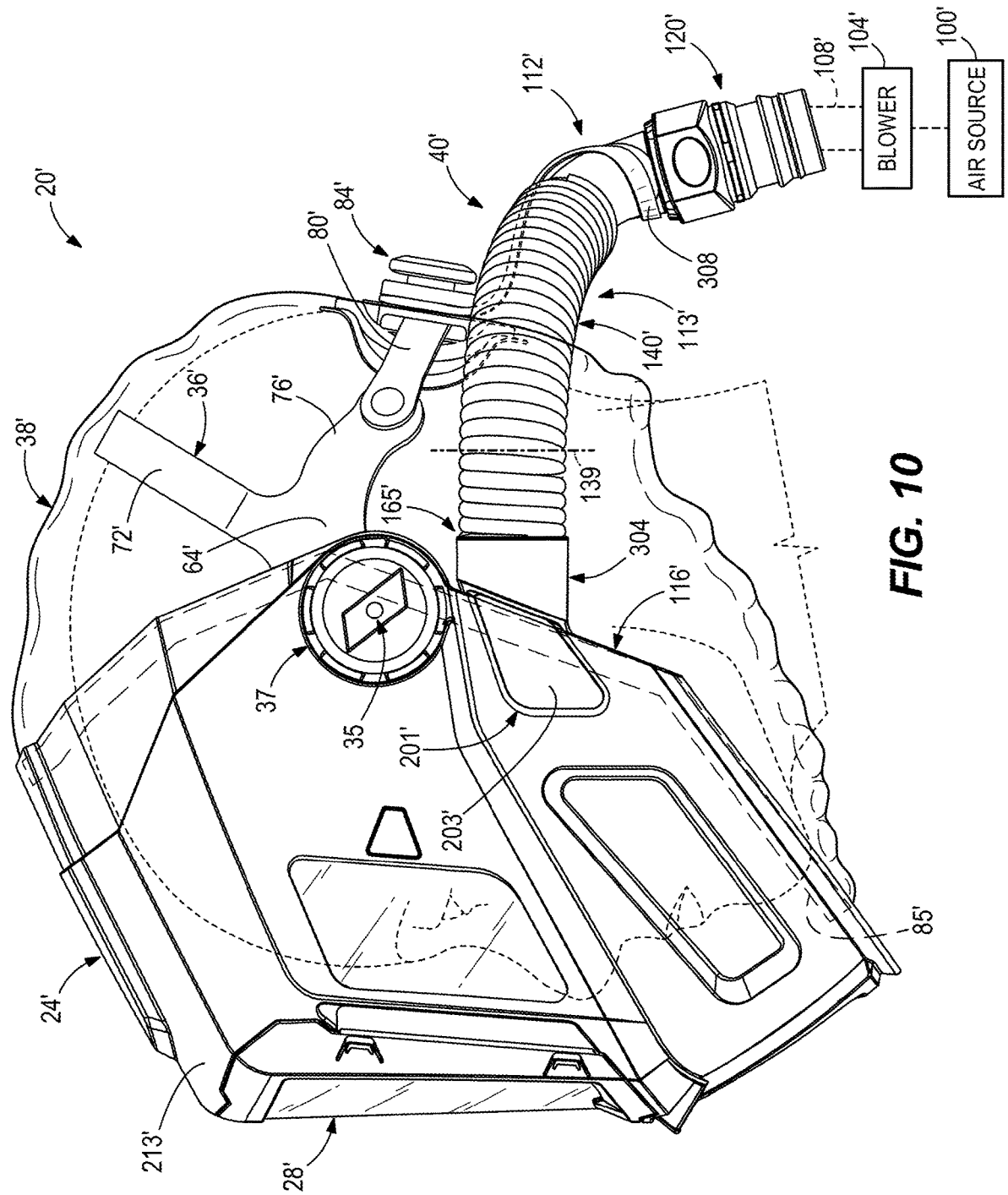
FIG. 10 is a side view of another example of protective headwear including another example of an airflow device for delivering air to an interior of the protective headwear, according to one aspect of the present disclosure.

With particular reference to FIG. 10, the exemplary headgear 36' is illustrated. Only a portion of and only one side of the headgear 36' is illustrated in FIG. 10, but it should be understood that the headgear 36' is a substantial mirror image about a vertical plane extending through a center of the headgear 36' (and a wearer's head when the headgear is worn) from a front of the protective headwear 20' to a rear of the protective headwear 20'. In other words, the headgear 36' is symmetrical on both sides of a wearer's head. The headgear 36' is capable of engaging a wearer's head and supporting the protective headwear 20' on the wearer's head. The headgear 36' may be coupled to the outer shell 24' of the protective headwear 20' in a variety of manners such as, for example, movably coupled, rigidly coupled, unitarily formed with, among other manners. In some examples, the outer shell 24' is coupled to the headgear 36' at a coupling location 35 near a side knob or adjustment knob 37, which is used to adjust the ease at which the outer shell 24' rotates relative to the headgear 36' between a lowered operating position (shown in FIG. 10) and a raised position (not shown, but conventional in the art). In other examples, the coupling location 35 may be at different positions relative to the outer shell 24' and the headgear 36'. It should be understood that the outer shell 24' may be coupled to the headgear in any of a wide variety of conventional manners and all of such possibilities are understood in the art.

In the illustrated example, the headgear 36' includes a side plate 64' on each side of the headgear 36', a forehead strap (not shown), a top strap 72', a rear strap 76', an occipital strap 80' and an adjustable member 84' coupled to the occipital strap 80'. In one example, the top strap 72' may be pivotally coupled at its ends to respective side plates 64' and may be positioned to extend over a crown or top of a wearer's head. In another example, the top strap 72' may be rigidly or unitarily formed as one-piece with the side plates 64'. In one example, the rear strap 76' may be pivotally coupled at its ends to respective side plates 64' and is positioned to extend around a rear of a wearer's head. In another example, the rear strap 76' may be rigidly or unitarily formed as one-piece with side plates 64'.

In one example, the occipital strap 80' may be pivotally connected at its ends to the side plates 64', may extend under the side plates 64' (i.e., between the side plates and a wearer's head), may drop down below the rear strap 76', and may wrap around or extend along the occipital crest of a wearer's head, then may extend under the occipital crest. In another example, the occipital strap 80' may be pivotally connected at its ends to the side plates 64', may be positioned externally of the side plates 64' (i.e., the side plates 64' are between ends of the occipital strap 80' and a wearer's head), may drop down below the rear strap 76', and may wrap around or extend along the occipital crest of a wearer's head, then may extend under the occipital crest.

The occipital strap 80' may assist with applying pressure, originating from the protective headwear 20', to be applied to bony structure (e.g., the occipital bone and crest of a skull) of the wearer's head where the wearer has less of a perception of pressure than on soft tissue of the wearer's head.

The illustrated example of the headgear 36' is provided to demonstrate at least some of the principles of the present disclosure and is not intended to be limiting upon the present disclosure. Rather, the protective headwear 20' may include any type of headgear and all such possibilities are intended to be with in the spirit and scope of the present disclosure.

With continued reference to FIG. 10, the head sleeve 38' is coupled to an interior surface 144' of the outer shell 24' and defines an opening 82' in a bottom thereof to allow a wearer's head to insert into and withdraw from an interior of the head sleeve 38' and an interior 116' of the protective headwear 20'. In the illustrated example, the head sleeve 38' includes elastic or other resilient member 83' around the opening to facilitate cinching or compression of the head sleeve 38' around a wearer's neck, thereby closing-off, eliminating or at least reducing the likelihood of air entering into or escaping from the interior 116' of the protective headwear defined by the head sleeve 38' and the outer shell 24'. In another example, the head sleeve 38' may include a drawstring around the opening to selectively open and cinch or close the opening.

The head sleeve 38' may be coupled to the outer shell 24' in a variety of manners. In one example, the head sleeve 38' is coupled to the interior surface 144' of the outer shell 24' with one or more coupling members 85'. In one example, the coupling member 85' may be a hook-and-loop type fastener. In other examples, the head sleeve 38' may be coupled to the interior surface 144' of the outer shell 24' in a variety of other manners including, but not limited to, snaps, screws, detents, buttons, adhesive, bonding, welding, or any other type of permanent, semi-permanent or removable manner, with all of such possibilities intended to be within the spirit and scope of the present disclosure.

The head sleeve 38' cooperates with the outer shell 24' to provide protection to a wearer's head and neck, along with providing an at least partially controlled environment in which the wearer's head is positioned. The controlled environment within the outer shell 24' and head sleeve 38' is at least partially controllable with respect to airflow within the protective headwear 20'. The airflow device 40' provides an airflow to the interior 116' of the protective headwear 20' to provide fresh, breathable air for the wearer while also controlling the temperature or at least the perception of temperature on a wearer's head due to convection. The head sleeve 38', outer shell 24', the controlled environment created therein, and the airflow device 40' provide a more comfortable environment within the protective headwear 20' when the protective headwear 20' may be worn in an uncomfortable environment.

Figure 11:
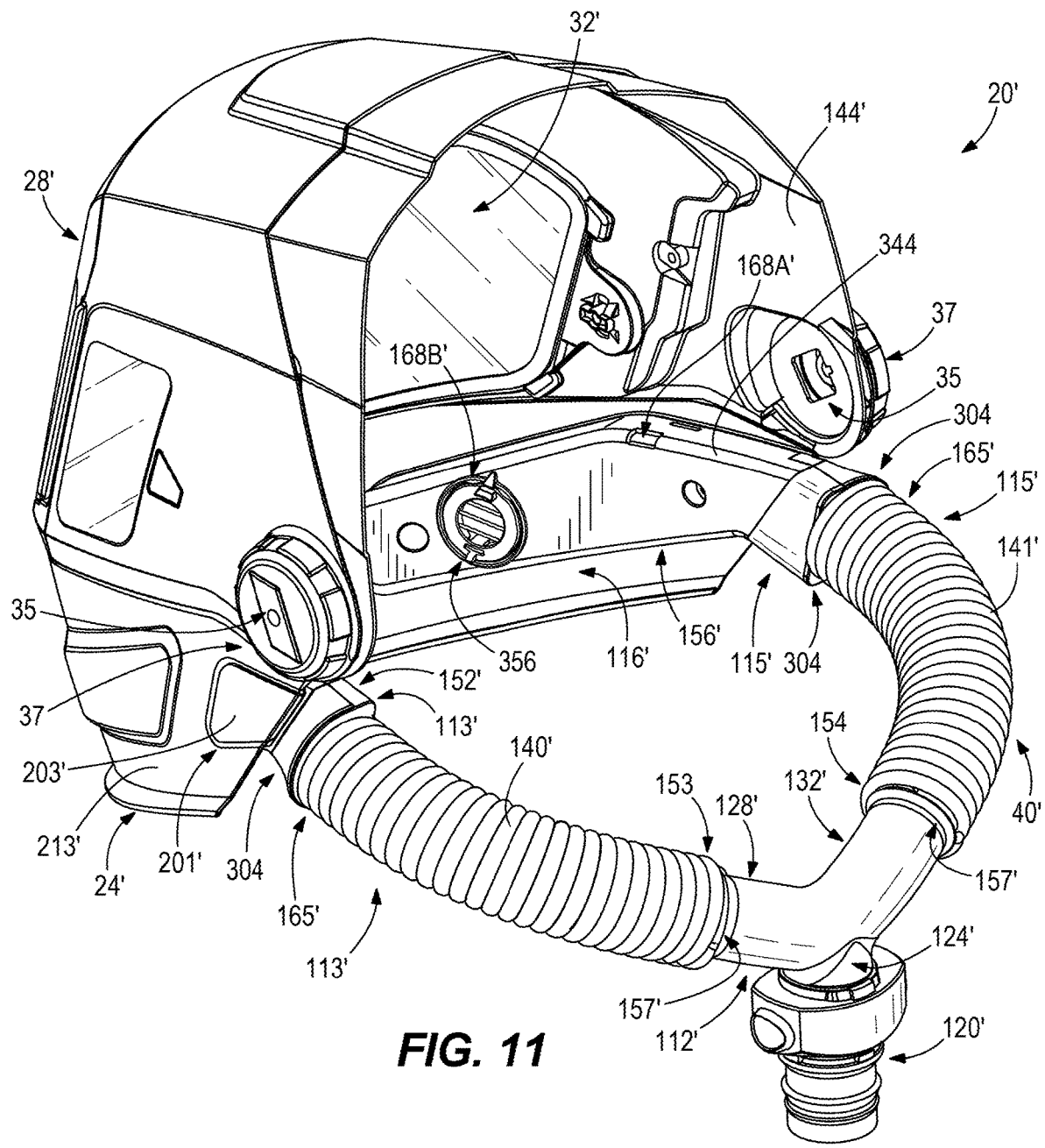
FIG. 11 is a rear perspective view of the protective headwear and airflow device shown in FIG. 10, in this view a head sleeve of the protective headwear is removed to facilitate viewing of the interior of the protective headwear, according to one aspect of the present disclosure.
Figure 12:
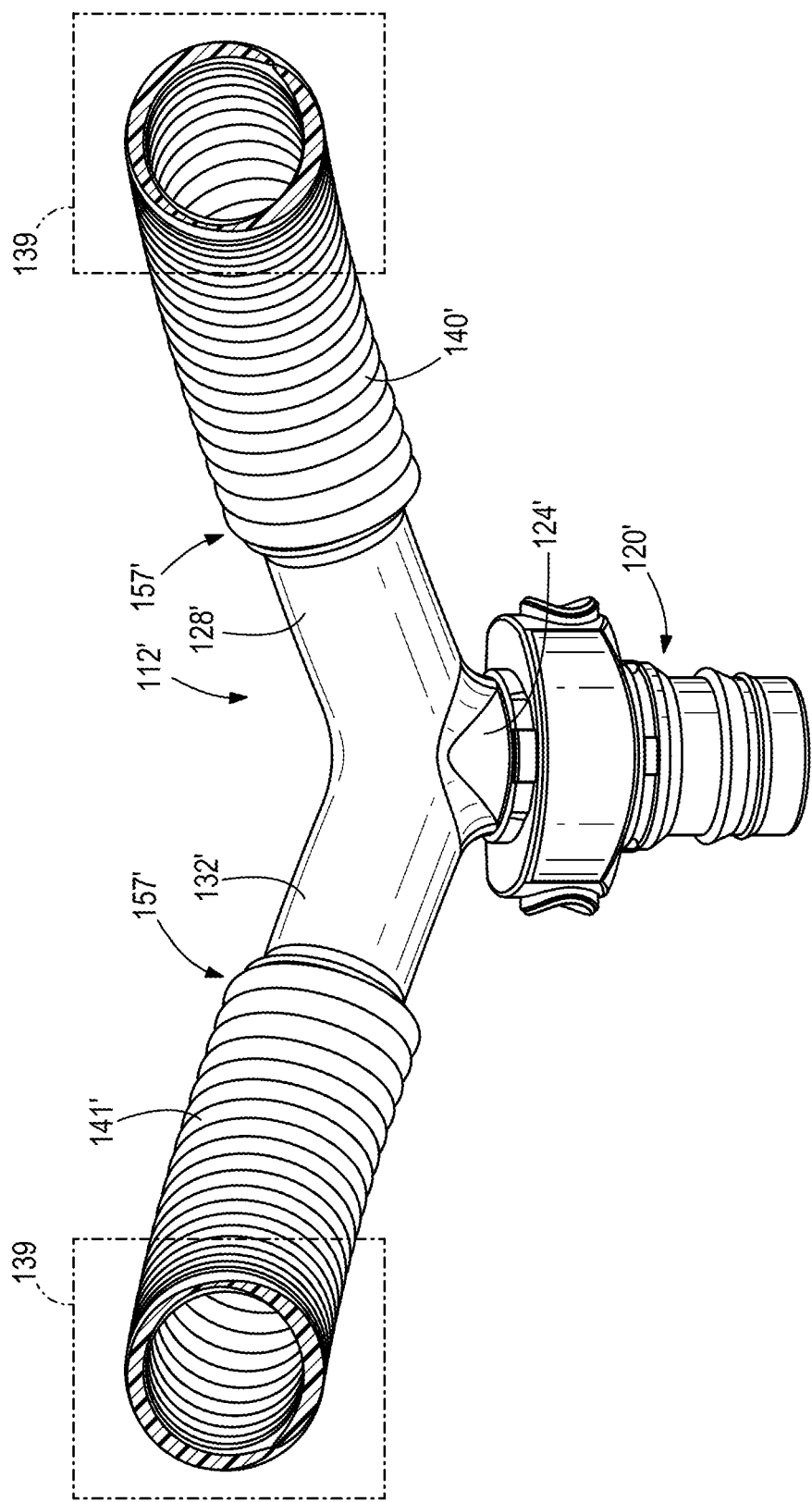
FIG. 12 is a front view of a portion of the protective headwear and airflow device shown in FIG. 10, according to one aspect of the present disclosure.
Figure 13:
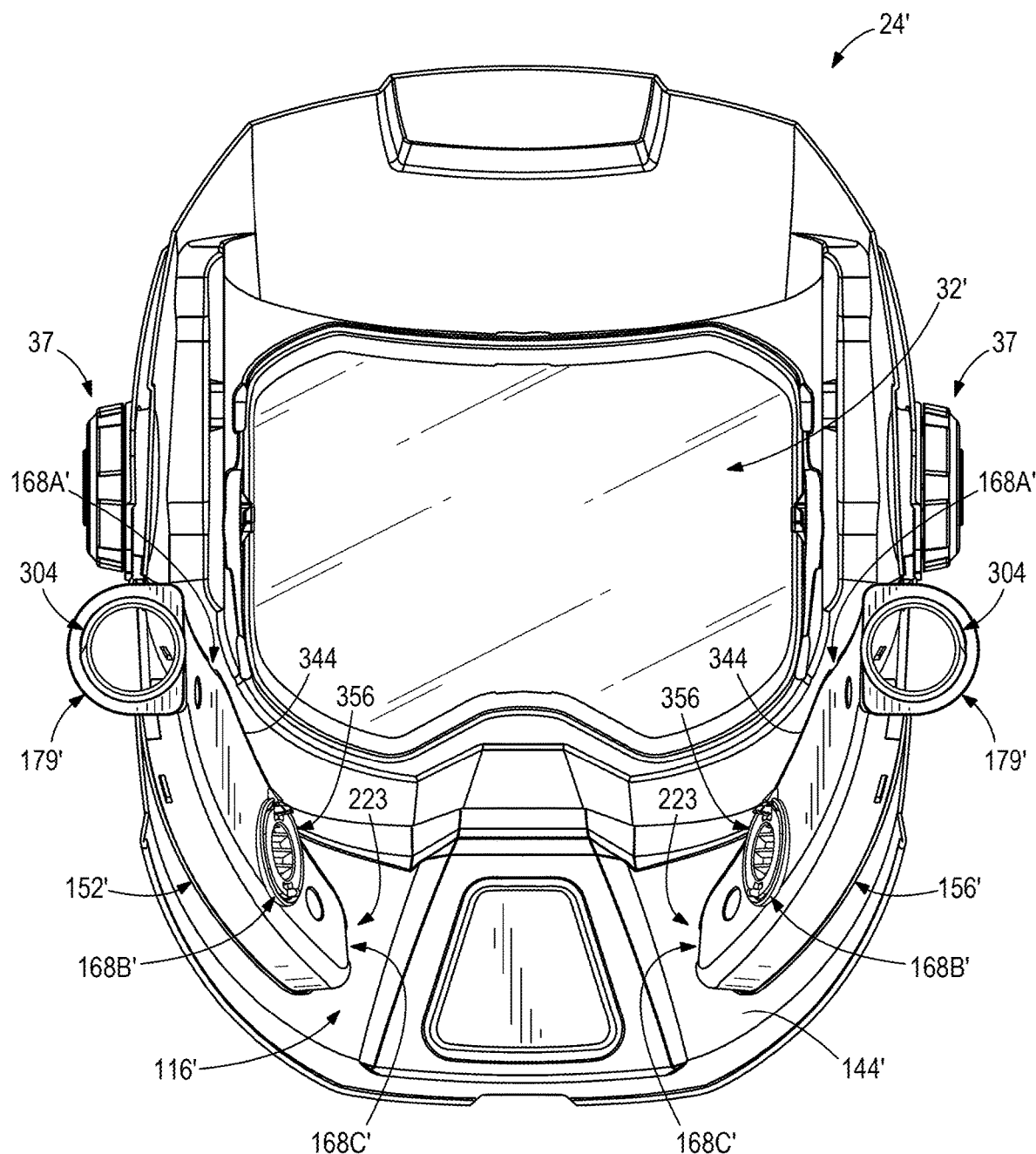
FIG. 13 is a rear view of a portion of the protective headwear and airflow device shown in FIG. 10, according to one aspect of the present disclosure.
Figure 14:
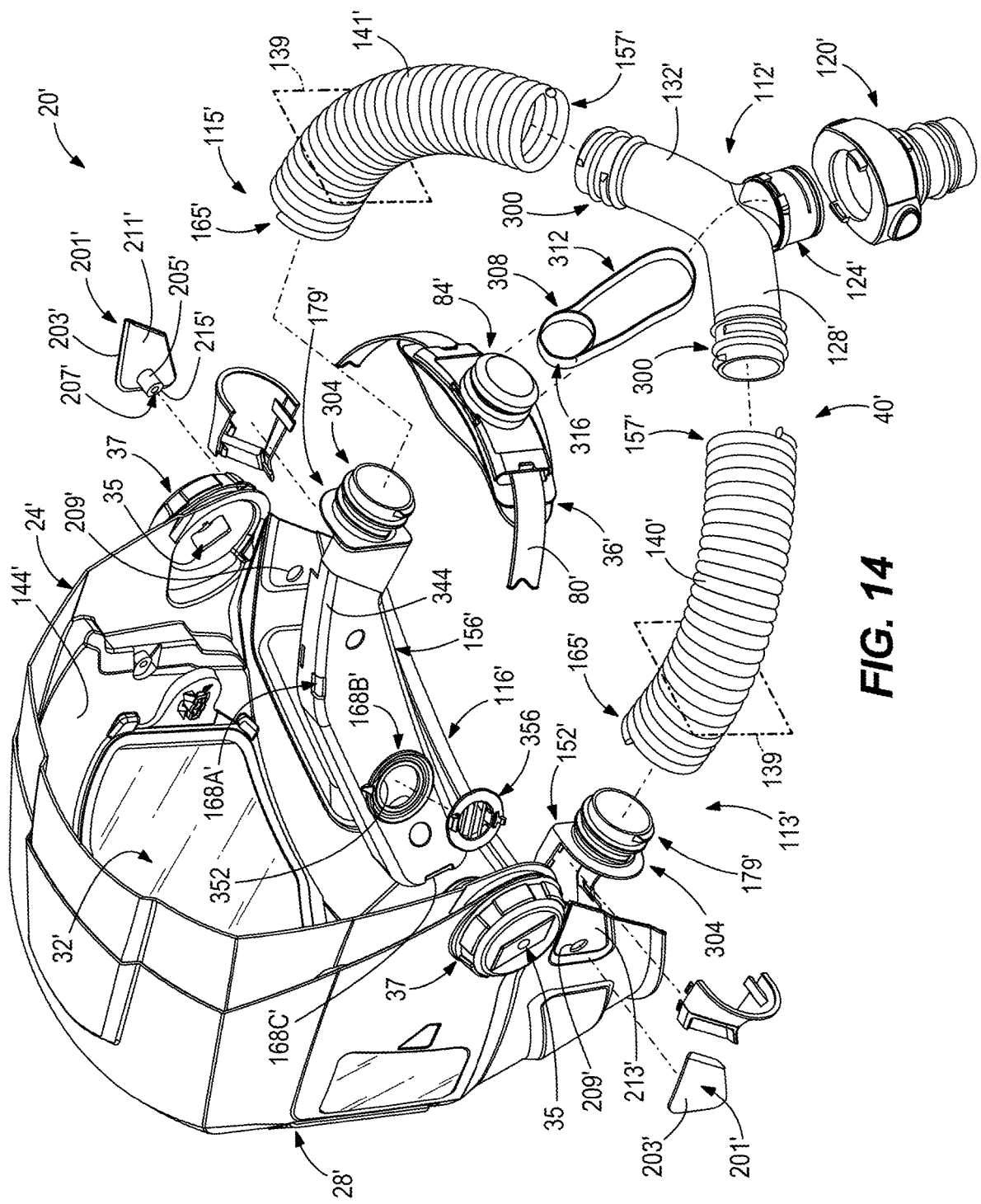
FIG. 14 is a rear, partially exploded, perspective view of the protective headwear and airflow device shown in FIG. 10, according to one aspect of the present disclosure.
Figure 15:
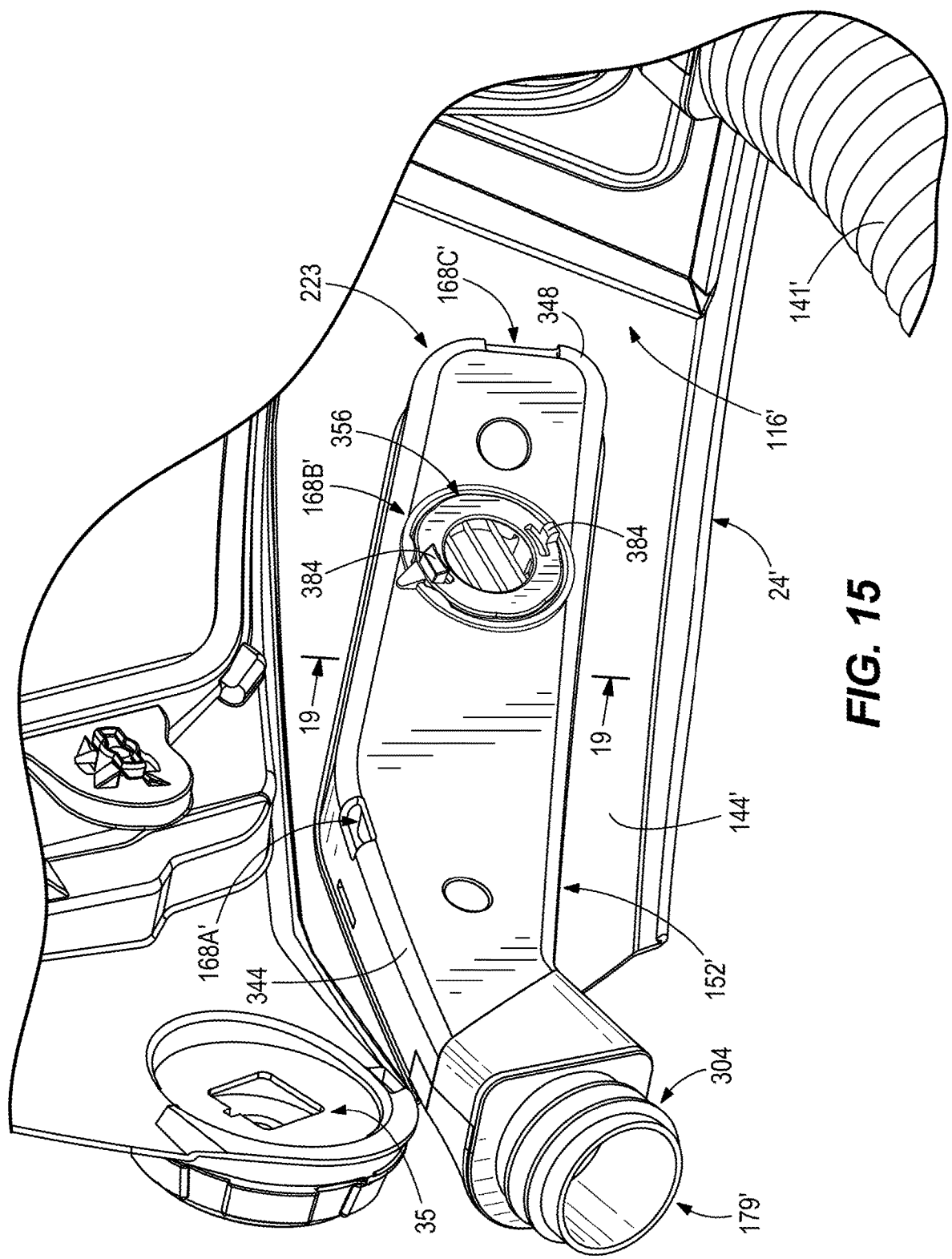
FIG. 15 is a rear perspective view of a portion of the protective headwear and airflow device shown in FIG. 10, in this view the head sleeve of the protective headwear is removed to expose the interior of the protective headwear and a plurality of air vents in the airflow device, according to one aspect of the present disclosure.
Figure 16:
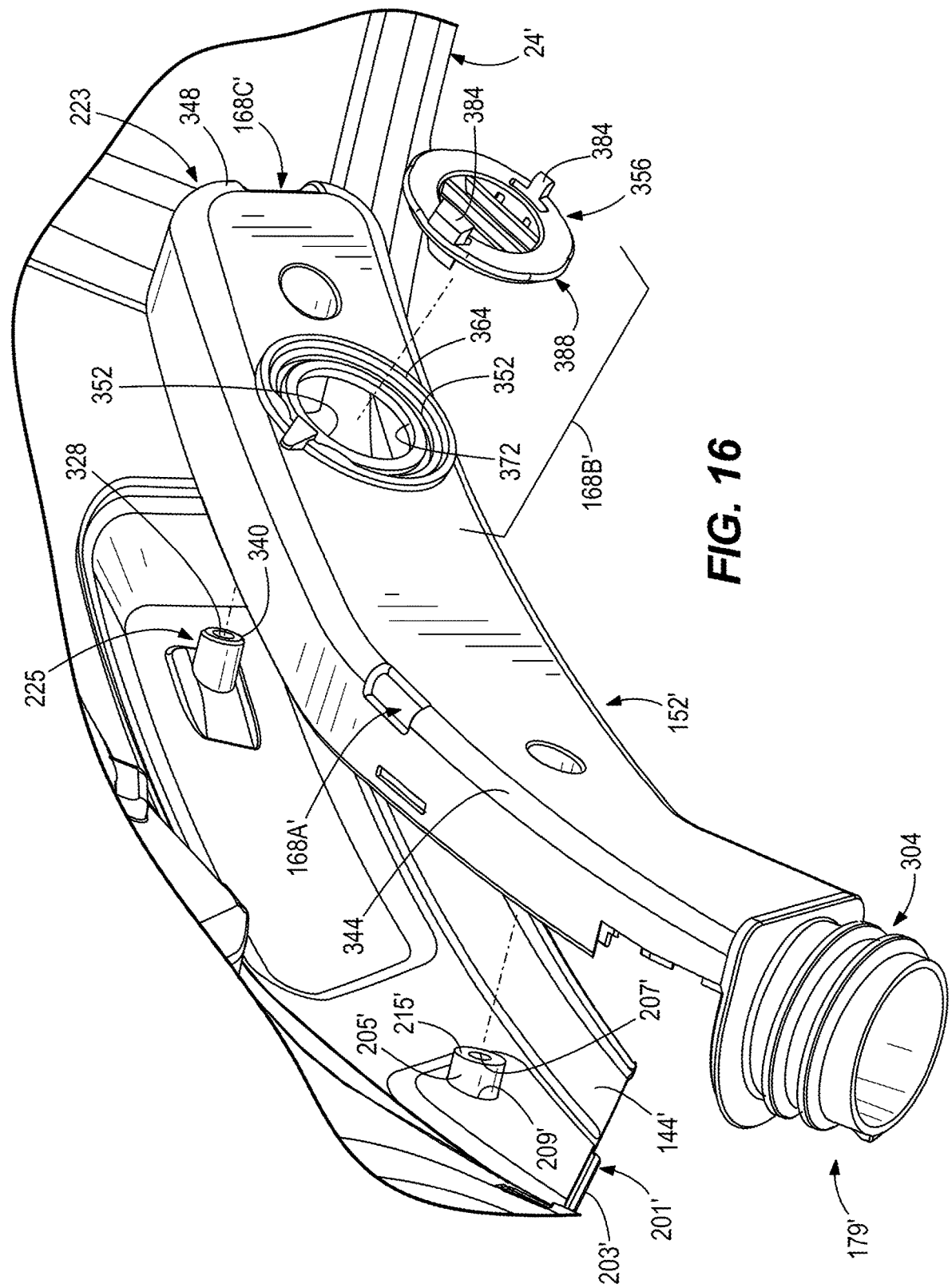
FIG. 16 is a rear, partially exploded, perspective view of the protective headwear and airflow device shown in FIG. 10, according to one aspect of the present disclosure.
Figure 17:
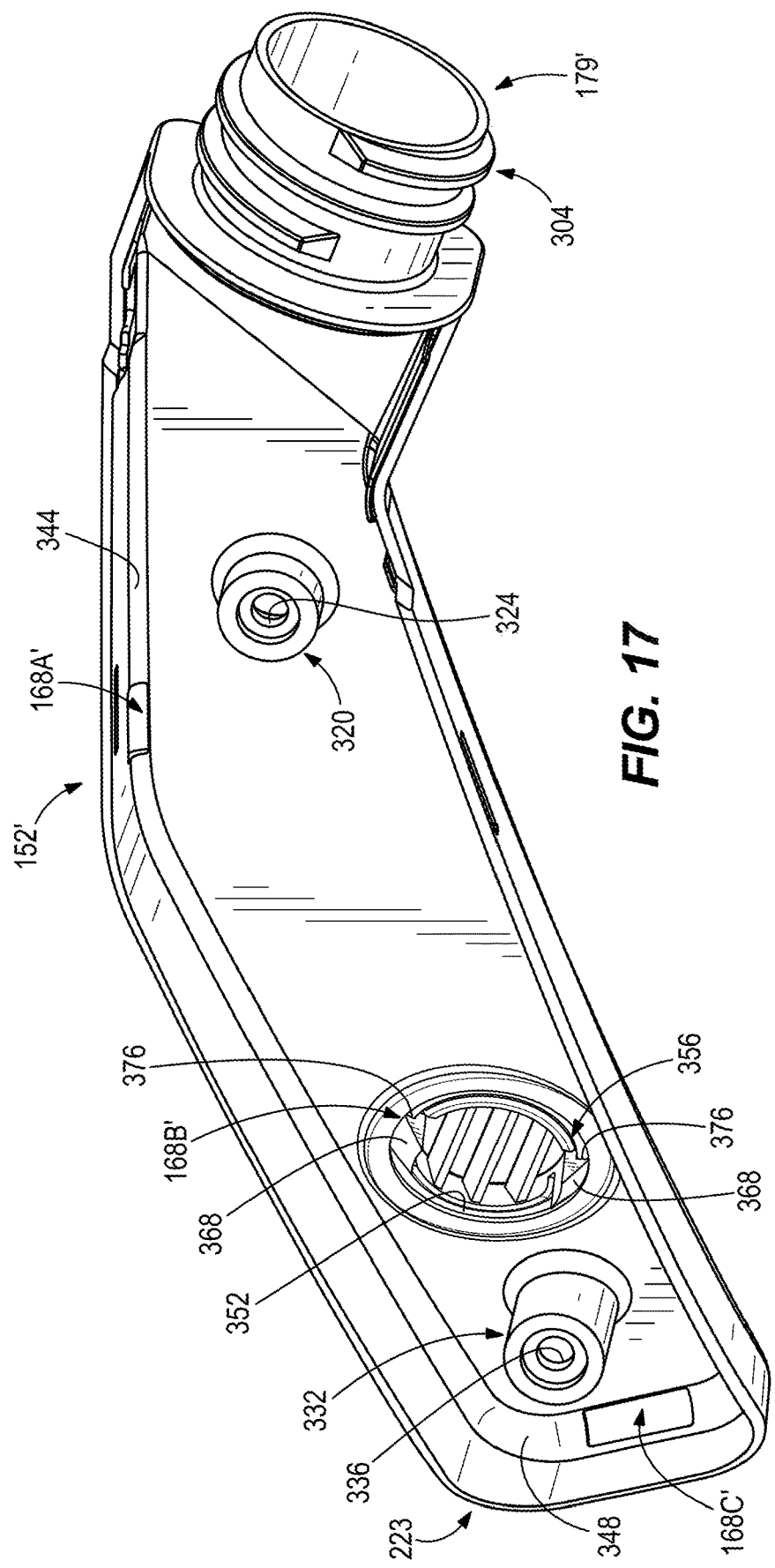
FIG. 17 is a perspective view of an interior of a portion of the airflow device shown in FIG. 10, in this view one example of air vent and one example of a manner of connection are illustrated, according to one aspect of the present disclosure.

With continued reference to FIGS. 10 and 11, the airflow device 40' includes an air source 100', a blower 104', a hose 108' or other air communication device, a manifold or coupling member 112', and a pair of ducts or tubes 113', 115' extending from the coupling member 112' to a location within the interior 116' of the protective headwear 20'. The blower 104' is in fluid communication with the air source 100' and blows air from the air source 100', through the hose 108', and into the coupling member 112', which is coupled to the protective headwear 20' to communicate air from the hose 108' to an interior space 116' within the outer shell 24' of the protective headwear 20'. The airflow device 40' may also include one or more filters for filtering the air prior to communication of the air to the interior space 116' of the protective headwear 20'.

The coupling member 112' includes an attachment member 120' at an end thereof for coupling the hose 108' to the coupling member 112'. The coupling member 112' defines an internal cavity therein for receiving air from the hose 108' and diverting the air downstream to the interior 116' of the protective headwear 20'. In the illustrated example, the coupling member 112' includes a "Y" shape comprising a receiving portion 124', a first diversion member 128' and a second diversion member 132' spaced-apart and extending away from the first diversion member 128'. The first diversion member 128' and the second diversion member 132' divide the airflow into two streams or portions and communicate the air along two downstream paths into respective first and second ducts 113', 115' and ultimately into different portions of the interior space 116' of the protective headwear 20'. In the illustrated example, the first and second diversion members 128', 132' are substantially circular in cross-section. Circular diversion members 128', 132' provide a more symmetrical flow of air therethrough versus other shapes such as, for example, square, rectangular, etc.

The first diversion member 128' is coupled to the first duct 113' and the second diversion member 132' is coupled to the second duct 115'. The first duct 113' is positioned along a first side of a wearer's head and the second duct 115' is positioned along a second side of the wearer's head opposite the first side.

In the illustrated example, the first duct 113' includes a first flexible portion or duct 140' and a first shell portion or duct 152', and the second duct 115' includes a second flexible portion or duct 141' and a second shell portion or duct 156'. In the illustrated example, the first and second flexible portions 140', 141' and the first and second shell portions 152', 156' are positioned below the coupling location 35 where the outer shell 24' couples to the headgear 36'. First ends 157' of the first and second flexible portions 140', 141' are respectively coupled to the first and second diversion members 128', 132'. The first and second flexible portions 140', 141' may be coupled to the first and second diversion members 128', 132' in a variety of manners and all manners are intended to be within the spirit and scope of the present disclosure. In the illustrated example, each of the first and second diversion members 128', 132' includes an engagement member 300 for engaging respective flexible portions 140', 141'. In the illustrated example, the engagement members 300 are external threads for engaging interior surfaces of the flexible portions 140', 141'. In other examples, the engagement members 300 (see FIG. 14) may be other types of engagement members having any size and configuration to sufficiently engage the interior surfaces of the flexible portions 140', 141' and facilitate coupling of the flexible portions 140', 141' to the coupling member 112'. In other examples, the flexible portions 140', 141' may be coupled to the coupling member 112' in any permanent, semi-permanent or selective manners and all of such possibilities are intended to be within the spirit and scope of the present disclosure.

Second ends 165' of the first and second flexible portions 140', 141' may be respectively coupled to the first and second shell portions 152', 156' in similar manners as the first ends 157' of the first and second flexible portions 140', 141' are coupled to the manifold or coupling member 112'. In the illustrated example, each of the first and second shell portions 152', 156' includes an engagement member 304 for engaging respective second ends 165' of the first and second flexible portions 140', 141'. In the illustrated example, the engagement members 304 are external threads for engaging interior surfaces of the flexible portions 140', 141'. In other examples, the engagement members 304 may be other types of engagement members having any size and configuration to sufficiently engage the interior surfaces of the flexible portions 140', 141' and facilitate coupling of the flexible portions 140', 141' to the first and second shell portions 152', 156'. In other examples, the flexible portions 140', 141' may be coupled to the first and second shell portions 152', 156' in any permanent, semi-permanent or selective manners and all of such possibilities are intended to be within the spirit and scope of the present disclosure.

In the illustrated example, the first and second flexible portions 140', 141' are substantially circular in cross-section along respective planes 139 (see FIGS. 10, 12 and 14) substantially perpendicular to longitudinal extents of the first and second flexible portions 140', 141'. Circular flexible portions 140', 141' provide a more symmetrical flow of air therethrough versus other shapes such as, for example, square, rectangular, etc.

With reference to FIGS. 10-14, ends 179' of the first and second shell portions 152', 156' are positioned externally, outside, behind or beyond an outermost edge of the outer shell 24'. Also, in the illustrated example, the first and second flexible portions 140', 141' are coupled to ends 179' of the first and second shell portions externally, outside, behind or beyond an outermost edge of the outer shell 24'. In the illustrated example, the head sleeve 38' defines a pair of apertures or openings (not shown, but may be similar to apertures or openings 181 in the protective headwear illustrated in FIGS. 1-7) through which the ends 179' of the first and second shell portions extend to facilitate the first and second ducts 113', 115' from passing from an exterior of the outer shell 24', through the head sleeve 38', and to the interior 116' of the protective headwear 20'.

The flexible portions 140', 141' allow the first and second ducts 113', 115' to be adjusted to accommodate movement of the outer shell 24' relative to the headgear 36' between a downward operating position and an upward inoperative position, heads of different sizes and shapes, different types of headgear, or other reasons. In some examples, the first and second ducts 113', 115' may not include a flexible portion and, instead, the first and second ducts 113', 115' may be completely rigid and extend from the manifold or coupling member 112' to their termination location within the outer shell 24'.

In the illustrated example, the airflow device 40' is coupled to the headgear 36' by a coupling member 308. The coupling member 308 may be any type of coupling member 308 and may have any size and configuration. In the illustrated example, the coupling member 308 is an elastic coupling member 308 positioned between an in engagement with the manifold or coupling member 112' and the headgear 36'. More particularly, the elastic coupling member 308 wraps around the coupling member 112' and wraps around the adjustable member 84'. In the illustrated example, the elastic coupling member 308 includes a first end comprising a first closed loop 312 coupled to and wrapped around the coupling member 112' and a second end comprising a second closed loop 316 coupled to and wrapped around the adjustable member 84'. The second closed loop 316 allows the elastic coupling member to selectively couple to and be uncoupled from the adjustable member 84' as desired, but ensures proper coupling during operation of the protective headwear 20'. In further examples, any portion(s) of the airflow device 40' may be coupled to any portion of the headgear 36'. It should be understood that the airflow device 40' may or may not be coupled to any other portion of the protective headwear 20' and all of such possibilities are intended to be within the spirit and scope of the present disclosure. The elastic properties of the coupling member 308 may provide a plurality of capabilities and/or functionalities. For example, the elasticity of the coupling member 308 allows a wearer to selectively couple and uncouple the coupling member 308 to and from the headgear 36' and coupling member 112'. Also, for example, the elasticity of the coupling member 308 facilitates movement of the coupling member 112' and other components of the airflow device 40' relative to the headgear 36', or vice versa, that may occur during use of the protective headwear 20'. Examples of such movement may include, but are not limited to, moving the outer shell 24' between upward and lowered positions, movement of the wearer's head relative to the coupling member 112' and flexible portions 140', 141' during use, other forces that may be applied to various components of the protective headwear 20' and/or airflow device 40' during use. Further, for example, the elasticity of the coupling member 308 applies a continuous force between the headgear 36' and the coupling member 112' to ensure the coupling member 112' and associated components of the airflow device 40' remain in close proximity of the headgear 36' and the remainder of the protective headwear 20'. In other words, the elastic coupling member 308 retains the coupling member 112' and associated components of the airflow device 40' to the remainder of the protective headwear 20'.

In the illustrated example, the coupling member 112' is positioned to a rear of a lower portion of a wearer's head or to a rear of the wearer's neck (see FIG. 10). The coupling member 112' may also be either spaced-apart from the headgear 36' and the wearer's lower head/neck or against at least one of the headgear 36' and a rear of the wearer's lower head/neck.

Referring now to FIGS. 10-19, the first shell portion 152' is coupled to and in fluid communication with the first flexible portion 140' to receive air from the coupling member 112' and the second shell portion 156' is coupled to and in fluid communication with the second flexible portion 141' to receive air from the coupling member 112'.

The first and second shell portions 152', 156' are similar in shape and configuration and it should be understood that the second shell portion 156' is a substantial mirror image of the first shell portion 152' about a vertical plane extending through a center of the protective headwear 20' from a front of the protective headwear 20' to a rear of the protective headwear 20'. In other words, in the illustrated example, the protective headwear 20' is symmetrical on both sides of a wearer's head. In another example, the protective headwear 20' may not be symmetrical on both sides and the first and second shell portions 152', 156' may not be substantially identical in shape and configuration. In a further example, the protective headwear 20' may include only one shell portion on only one side of the protective headwear 20'. In such an example, the coupling member 112' may only include a single diversion member (or no diversion member because it may not be necessary to divert, divide or separate the air flow) coupled to and in fluid communication with the single shell portion. In still another example, the protective headwear 20' may include more than two shell portions. In such an example, the coupling member 112' may include a complementary number of diversion members to couple to and be in fluid communication with the plurality of shell portions included in the protective headwear 20'. Additionally, in such an example, the first and second ducts 113', 115' may include a complimentary number of flexible portions to couple the manifold or coupling member 112' to the shell portions.

Returning to the illustrated example and to FIGS. 10-19, the first and second shell portions 152', 156' are coupled to the outer shell 24'. The first and second shell portions 152', 156' may be coupled to the outer shell 24' in a variety of manners and all possibilities are intended to be within the spirit and scope of the present disclosure. For example, the first and second shell portions 152', 156' may be coupled to the outer shell 24' by fastening, bonding, welding, unitarily forming as one-piece with, friction-fit, interference-fit, tongue and groove, detent, snap-fit, hook and loop type fastening, or any other manner of permanently, semi-permanently, or removably coupling.

In the illustrated example, the first and second shell portions 152', 156' are coupled to the outer shell 24' in similar manners and, therefore, only coupling of the first shell portion 152' will be described with it being understood that the description may apply mutatis mutandis to coupling the second shell portion 156' to the outer shell 24'. In other examples, the first and second shell portions 152', 156' may be coupled to the outer shell 24' in different manners.

With reference to FIGS. 10-19, the protective headwear 20' includes a coupling member 201' including a base 203' and a projection 205' extending from the base 203'. An aperture 207' is defined in the projection 205'. The outer shell 24' defines an aperture 209' therein configured to receive the projection 205'. With the projection 205' inserted into the aperture 209' and an interior surface 211' of the base 203' engaging an outer surface 213' of the outer shell 24', end 215' of the projection 205' is positioned in the interior 116' of the outer shell 24'. The first shell portion 152' includes a projection 320 and an aperture 324 defined therein. The projection 320 engages the end 215' of the projection 205' and apertures 207', 324 align with one another. A fastener (not shown) is inserted into the aligned apertures 207', 324 to couple the first shell portion 152' to the outer shell 24'. The first shell portion 152' is also coupled to the outer shell 24' near a second end 223 of the first shell portion 152'. A projection 225 (see FIG. 16) extends from the interior surface 144' of the outer shell 24' and the projection 225 defines an aperture 328 therein. The first shell portion 152' includes a projection 332 and an aperture 336 defined therein. The projection 332 engages end 340 of the projection 225 and apertures 328, 336 align with one another. A fastener (not shown) is inserted into the aligned apertures 328, 336 to couple the first shell portion 152' to the outer shell 24'.

Figure 19:
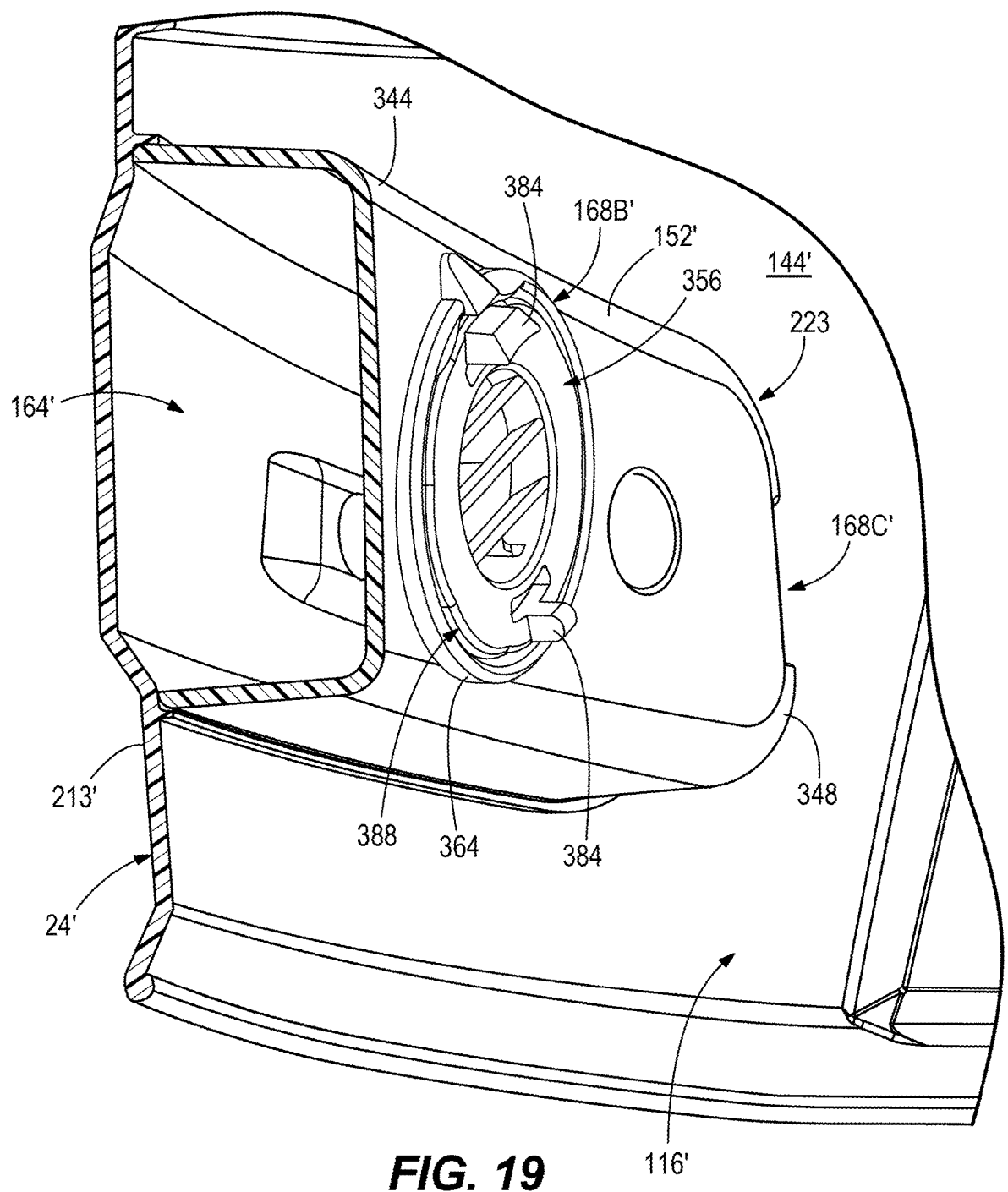
FIG. 19 is a cross-sectional view taken along line 19-19 in FIG. 15, according to one aspect of the present disclosure.

With particular reference to FIG. 19, an airflow path or duct cavity 164' is defined along each of two sides of the interior surface 144' of the outer shell 24' (right side and left side of interior surface of the outer shell) by a combination of the first and second shell portions 152', 156' and the interior surface 144' of the outer shell 24'. Three sides of each duct cavity 164' are defined by the respective first or second shell portion 152', 156' and a fourth side of each duct cavity 164' is defined by the interior surface 144' of the outer shell 24'.

Referring now to FIGS. 11 and 13-20, each of the first and second shell portions 152', 156' includes a plurality of exhaust ports 168' configured to exhaust air from the first and second shell portions 152', 156' to the interior space 116' of the protective headwear 20'. In the illustrated example, each shell portion 152', 156' includes three exhaust ports 168A', 168B', 168C'. Alternatively, the shell portions 152', 156' may include any quantity of exhaust ports and be within the spirit and scope of the present disclosure. In the illustrated example, exhaust ports 168A', 168C' have a different shape than exhaust port 168B'. In the illustrated example, the three exhaust ports 168A', 168B', and 168C' are located below the coupling location 35 where the outer shell 24' couples to the headgear 36'. In this illustrated example, exhaust ports 168A', 168C' are generally rectangular in shape and exhaust port 168B' is generally round in shape. It should be understood that the exhaust ports may have any shape, may be different in shape relative to each other in any combination, or may all be similar in shape, and all of such possibilities are intended to be within the spirit and shape of the present disclosure. Returning to the illustrated example, exhaust port 168B' is independently adjustable to selectively alter a directional flow of the air exhausting from the exhaust port 168B', and exhaust ports 168A' and 168C' are fixed and not adjustable. It should be understood that any number of the exhaust ports 168' may be adjustable, rigid and non-adjustable, and any combination thereof and all of such possibilities are intended to be within the spirit and scope of the present disclosure.

In the illustrated example, the exhaust port 168A' is defined in a top, corner edge 344 of each of the first and second shell portions 152', 156'. The top, corner edge 344 is located on the top surface of each of the first and second shell portions 152', 156' at the top, corner edge closest to a wearer's face or, in other words, the top, corner edge spaced furthest from the interior surface of the outer shell 24'. Positioning the exhaust port 168A' in this location exhausts air in an upward and inward manner (inward may be defined as toward a user's face). In other examples, the exhaust port 168A' may be defined in different positions on the first and second shell portions 152', 156'.

In the illustrated example, the exhaust port 168C' is defined in a front, corner edge 348 of each of the first and second shell portions 152', 156'. The front, corner edge 348 is the front, corner edge closest to a wearer's face or, in other words, the front, corner edge spaced furthest from the interior surface of the outer shell 24'. Positioning the exhaust port 168C' in this location exhausts air in a forward and inward manner (inward may be defined as toward a user's face).

In one example, the adjustable exhaust port 168B' may be adjustable along multiple axes. In another example, the adjustable exhaust port 168B' may be adjustable along two axes. In a further example, the adjustable exhaust port 168B' may be adjustable along three axes. The illustrated example provides adjustable exhaust port 168B' with adjustability along three axes. The direction of the exhaust port 168B' may be adjusted to accommodate varying sizes and shapes of wearers' faces, variance in environments in which the protective headwear 20' may be used, and accommodate wearer's preferences with respect to where and how they desire airflow to impact their face.

In the illustrated example, each of the adjustable exhaust ports 168B' is comprised of an exhaust aperture 352 defined in the respective one of the first and second shell portions 152', 156' and a damper or baffle 356 positioned in exhaust aperture 352. The first and second shell portions 152', 156' each define a recess 360 surrounding or encircling the aperture 352 and a lip or projection 364 surrounding or encircling the aperture 352 and the recess 360. In the illustrated example, the baffle 356 includes a pair of coupling tabs or members 368 for selectively coupling the baffle 356 to a respective one of the first and second shell portions 152', 156' in the respective aperture 352. The coupling tabs 368 are resilient and include a ramped or angled surface to allow the coupling tabs 368 to deflect upon engagement with a surface 372 of the shell portions 152', 156' defining the apertures 352, pass by the surface 372 and return toward their shape prior to deflection. Each of the coupling tabs 368 includes a projection or lip 376 that engages the respect surface 372 of the respective shell portions 152', 156' to secure the baffle 356 to the respective shell portion 152', 156'. In the illustrated example, the baffle 356 further includes a pair of actuating members 384 that are engageable by a wearer to move or rotate the baffle 356 relative to the respective one of the shell portions 152', 156'. Movement or rotation of the baffle 356 relative to the respective one of the shell portions 152', 156' adjusts the airflow exhausted therethrough along three axes (see representative, but not limiting, axes in FIG. 20).

In one example, the baffle 356 may rotate freely and in an unobstructed manner within the aperture 352. That is, there is no substantive friction or resistance to rotation of the baffle 356 within the aperture 352. In another example, the aperture 352 and the baffle 356 may be complementarily shaped to provide a sufficient amount of friction or resistance between the baffle 356 and the respective one of the shell portions 152', 156' to prevent free rotation of the baffle within the aperture under the effects of gravity or forces experienced during use/operation of the protective headwear 20'. In a further example, the baffle 356 may be positively secured in one or more positions within the aperture 352 and relative to the respective one of the shell portions 152', 156'. In such an example, one or more of the baffle 356, aperture 352 and/or the shell portions 152', 156' may include structure that positively secures the baffle 356 in one or more positions.

Figure 18:
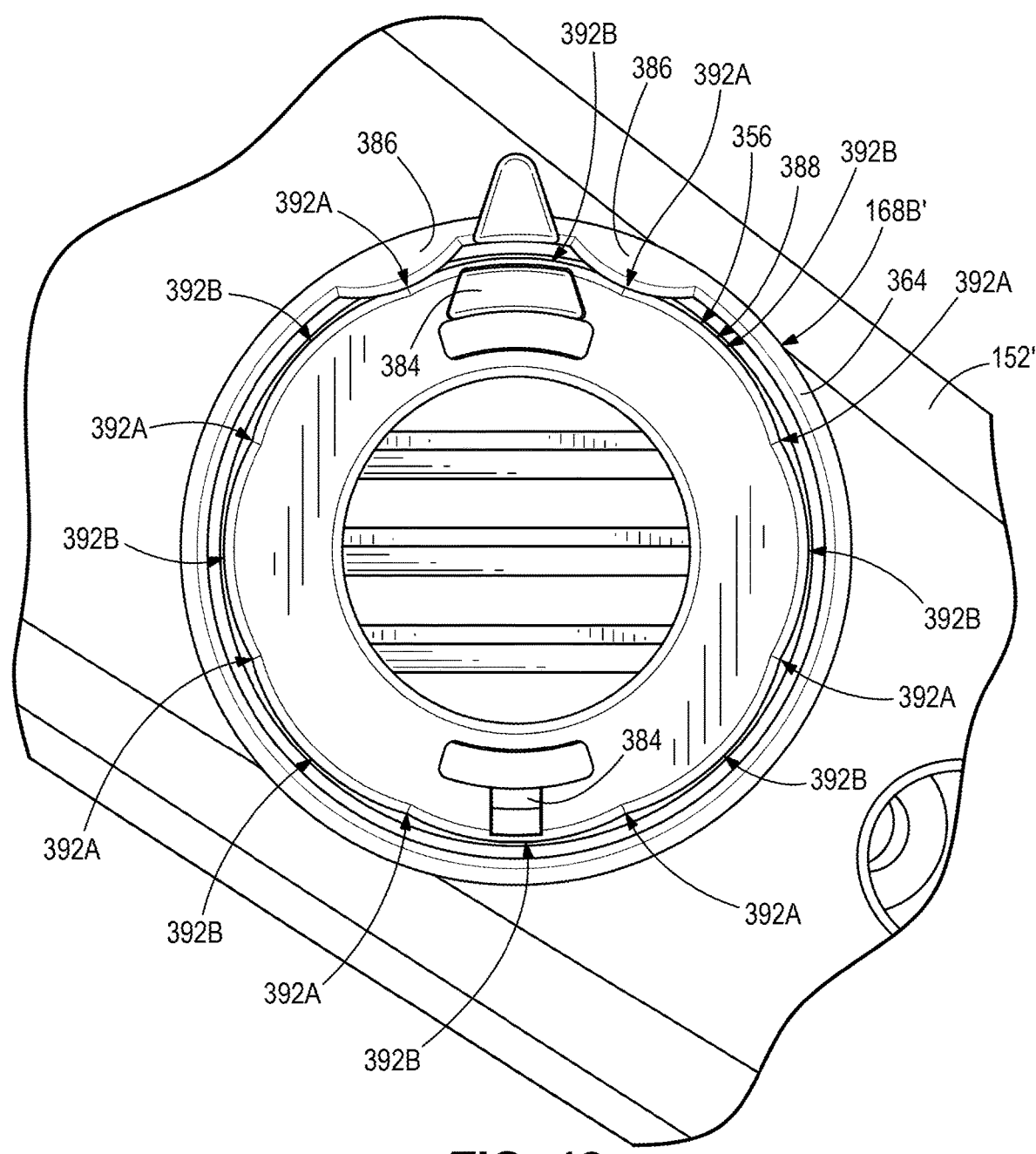
FIG. 18 is an elevational view of the air vent shown in FIG. 17, according to one aspect of the present disclosure.

With particular reference to FIG. 18, the baffle 356 is configured to be positively secured in a plurality of positions relative to the aperture 352 and the respective one of the shell portions 152', 156'. In the illustrated example, the baffle 356 includes a perimeter 388 having a plurality of securement features 392 and the lip 364 includes one or more securement features 386 complementarily configured to cooperate with the securement features 392 of the baffle 356 to selectively, positively secure the baffle 356 relative to the aperture 352 and a respective one of the shell portions 152', 156' in a plurality of positions. In the illustrated example, the securement features 392 of the baffle 356 may be considered a scallop shape defined in the perimeter 388 of the baffle 356. Alternatively, the securement features 392 of the baffle 356 may be considered a plurality of alternating projections separated by a plurality of alternating recesses or indentations. In the illustrated example, the securement features 386 of the lip 364 are comprised of a pair of projections configured to engage the perimeter 388 of the baffle 356. The baffle 356 is positively secured in a position when the projections 386 on the lip 364 are positioned in the recesses 392A defined in the perimeter 388 of the baffle 356. Rotation of the baffle 356 moves the perimeter 388 of the baffle 356 relative to the projections 386 on the lip 364, which brings the projections 392B on the perimeter 388 of the baffle 356 into alignment with the projections 386 on the lip 364. When the projections 386, 392B are aligned, the baffle 356 is not positively secured in place. The baffle 356 must be rotated further until the recesses 392A are aligned with the projections 386 and the projections 386 are positioned in the recesses 392A. It should be understood that the illustrated example of positively securing the baffle 356 is only one example and is not intended to be limiting upon the present disclosure. Rather, many other examples of positively securing the baffle 356 are contemplated and are intended to be within the spirit and scope of the present disclosure. For example, the securement features of the baffle and the lip or duct may be reversed. That is, an interior surface of the lip may include the scallop shaped comprised of a plurality of alternating projections and recesses and the perimeter of the baffle may include one or more projections to interact with the scallop shape in the lip. Also, for example, the lip and/or the perimeter of the baffle may include any number of projections and recesses.

Figure 20:
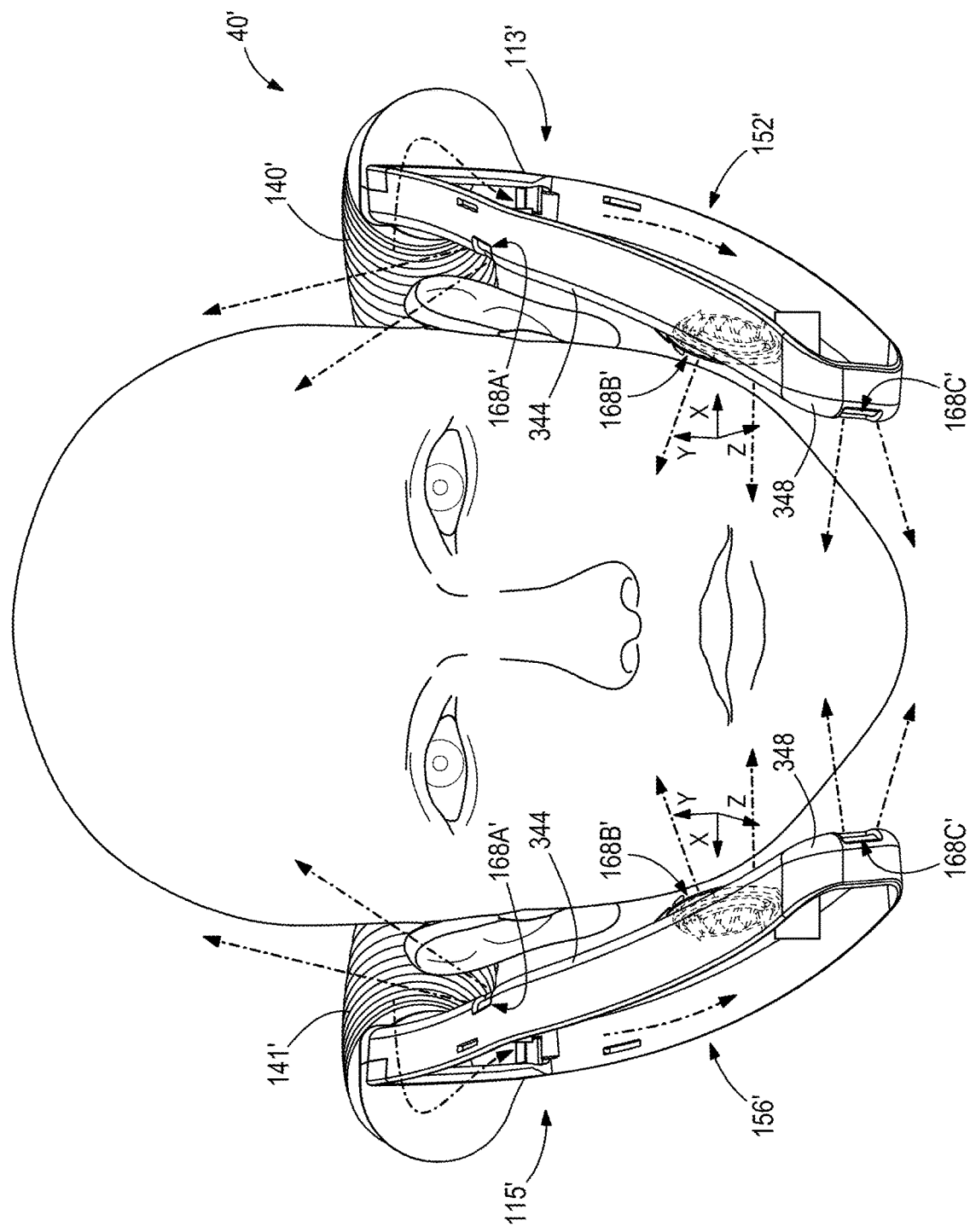
FIG. 20 is a front view of a portion of the airflow device shown in FIG. 10 with one example of an environment with which the airflow device may be associated, this view shows the airflow device directing airflow on a wearer's face without directing the airflow into the wearer's eyes, according to one aspect of the present disclosure.
Figure 21:
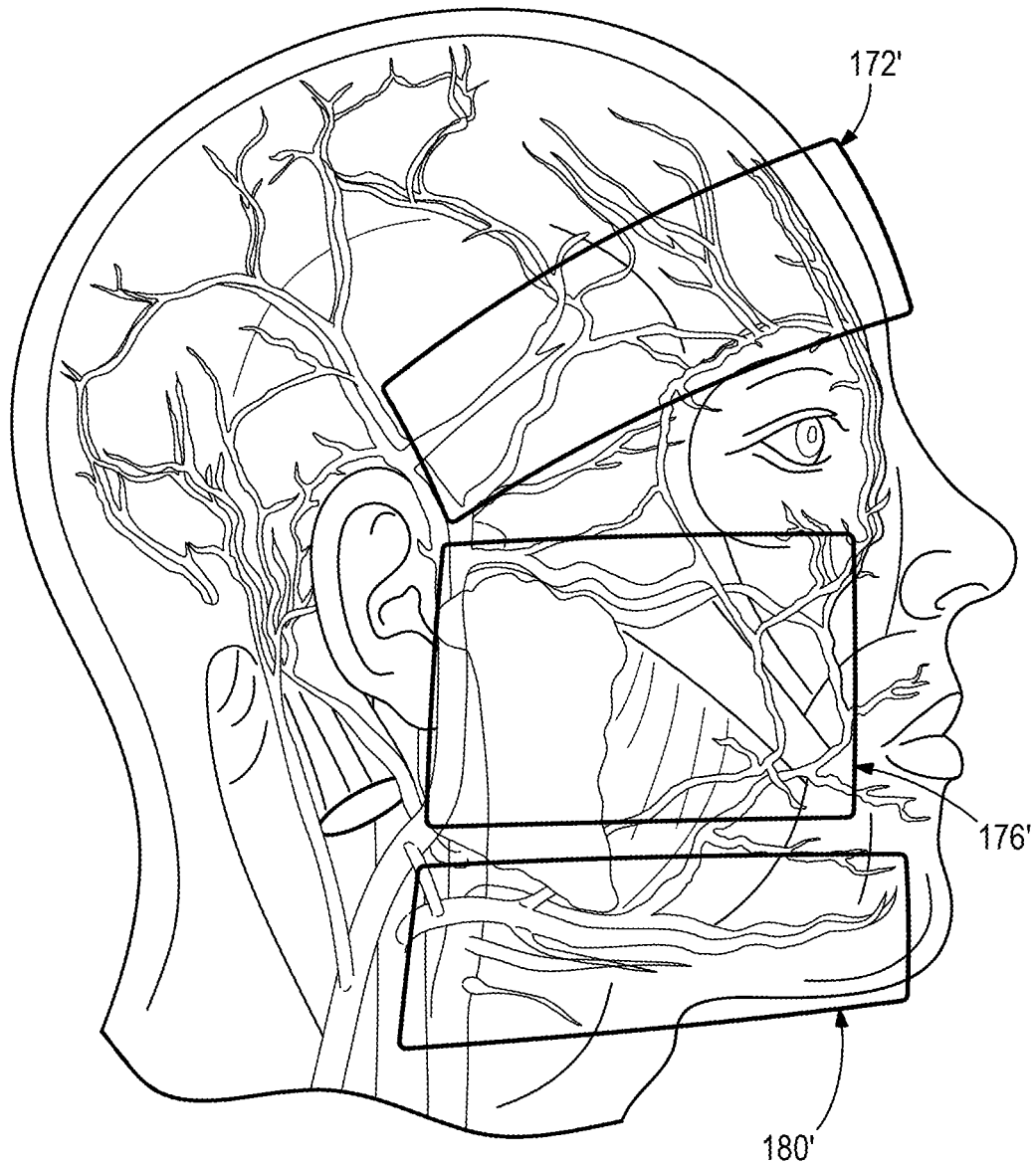
FIG. 21 is a diagram of another example of an environment with which the airflow device may be associated, according to one aspect of the present disclosure.

With continued reference to FIGS. 10-19 and additional reference to FIGS. 20 and 21, the exhaust ports 168' are positioned along the first and second shell portions 152', 156' to supply air to particular portions of the wearer's head. In the illustrated example, top exhaust ports 168A' supply air to first zones 172' (one on each side of the wearer's head), middle exhaust ports 168B' supply air to second zones 176' (one on each side of the wearer's head), and bottom exhaust ports 168C' supply air to third zones 180' (one on each side of the wearer's head). In one example, the first zones 172' generally correspond to temples and/or a forehead of the wearer's head, second zones 176' generally correspond to cheeks of the wearer's head, and third zones 180' generally correspond to jaw and/or neck areas of the wearer's head. In other examples, the zones may correspond to other portions of a wearer's head.

In the illustrated example, the exhaust ports 168' may be positioned to exhaust air generally perpendicular to the portions or zones of the wearer's head associated with the exhaust ports 168'. Exhausting air at an angle generally perpendicular to the associated portion of the wearer's head generates more turbulence (compared to a laminar exhaust stream when air is delivered parallel or generally parallel to a portion of the wearer's head) when the exhaust stream engages the portion of the wearer's head.

In one example, the zones or portions of the wearer's head may be determined based on those areas of a wearer's head that have a higher perception of airflow and cooling. For example, a human face has certain areas with large concentrations of superficial blood vessels such as temples, forehead, cheeks, jaw and neck. Additionally, it is important to avoid blowing air directly into a wearer's eyes in order to avoid drying a wearer's eyes or otherwise deteriorating a wearer's comfort level. Moreover, exhausting airflow in the manner performed by the present disclosure may blow air onto a larger percentage of the wearer's face than conventional airflow, which is blown from a location above the wearer's forehead straight down over the wearer's face and into the wearer's eyes.

In some examples, a velocity and/or an angle at which air exhausts from the exhaust ports 168' may be adjusted. For example, the position and/or exhaust apertures associated with the exhaust ports 168' or the exhaust ports 168' themselves may be adjusted to adjust the exhaust velocity and/or direction of the air (as described above), the coupling member 112' may include an actuator, damper and/or baffle that may be actuated to adjust the exhaust velocity and/or angle of the air, the blower 104' may be adjusted to adjust the exhaust velocity and/or angle of the air, or any of a wide variety of other manners of adjusting air velocity and/or air angle are possible, and all of such possibilities are intended to be within the spirit and scope of the present disclosure. With particular reference to exhaust port 168B', the baffle 356 is moveable to adjust airflow traveling through the exhaust port 168B'. In some examples, one or more of exhaust ports 168A', 168C' may include a similar or different movable baffle to adjust airflow there through.

The components of the present disclosure utilized to communicate air to an interior space 116' of the protective headwear 20' are coupled and positioned relative to the protective headwear 20' to locate a center of gravity in a more ideal location relative to a wearer's head, thereby decreasing the level of stress and pressure applied to a wearer's head. For example, the manifold or coupling member 112' of the airflow device 40' is positioned near or to a rear of the protective headwear 20' generally below a wearer's head and behind a wearer's neck, thereby adding weight to a rear of the protective headwear 20' behind a wearer's neck and biasing or positioning the center of gravity of the overall protective headwear 20' and airflow device 40' in a low, rearward direction. Positioning weight behind a wearer's head and/or neck and below a wearer's head via the manifold 112', and positioning portions of the first and second ducts 113', 115' low and alongside a wearer's head offsets weight in front of the wearer's head provided by the outer shell 24' and shields. Moreover, the flexible portions 140', 141' extend from the manifold 112' toward the outer shell 24' and connect to the first and second shell portions 152', 156' below the coupling location 35 where the outer shell 24' couples to the headgear 36'. During welding or other operating process, a wearer may be looking forward and downward, thereby shifting the center of gravity forward of a middle of the wearer's head. By locating the coupling member 112' and associated components at a rear of the protective headwear 20' behind the wearer's head and/or neck, the coupling member 112' and other air communication components (e.g., the flexible portions 140', 141') contribute to positioning the center of gravity more towards a rear of the protective headwear 20' than it would otherwise be without the coupling member 112' and other air components being positioned where they are. Additionally, the first and second shell portions 152', 156' are minimal in size, weight and profile, and are appropriately positioned to contribute to a more ideal location of the center of gravity. In some examples, a more ideal location of the center of gravity of the protective headwear 20' is over a middle or mid-line of the wearer's head, thereby decreasing any unnecessary torque applied to a wearer's head and neck by having the center of gravity located toward a front or a rear of the protective headwear 20'. Furthermore, extending one helmet duct along each side of the protective headwear 20' and below a wearer's ears (compared to a single large duct over a top of a wearer's head) requires less material, thereby reducing the overall weight of the protective headwear 20'. One example of a net effect of the components associated with providing airflow to an interior 116' of the protective headwear 20' will be to position the center of gravity closer to a mid-line of the wearer's head.

With continued reference to FIGS. 10-19, positioning the first and second shell portions 152', 156' below a wearer's ears and/or near a bottom edge of the outer shell 24' also facilitates a low position of the flexible portions 140', 141' and the coupling member 112' relative to the protective headwear 20'. As indicated above, the outer shell 24' is capable of being moved between an upward position and a lowered operating position. In the upward position, the outer shell 24' is rotated upward and rearward. By coupling the flexible portions 140', 141' to the first and second shell portions 152', 156' at a low position or lower half of the protective headwear 20', the flexible portions 140', 141' will not provide significant resistance to or obstruct rotation of the outer shell 24' from the lowered position to the upward position. Additionally, the flexible portions 140', 141' will not interfere or get in the way of the outer shell 24' as it rotates between positions. The coupling member 112' also will not provide significant resistance to or obstruct the outer shell 24' as it rotates between positions. Since the shell portions 152', 156', flexible portions 140', 141' and coupling member 112' are all positioned low and/or on the lower half of the protective headwear 20' and do not obstruct movement of the outer shell 24', these components are capable of having configurations that optimize performance rather than configurations that avoid obstruction of the outer shell 24'. Accordingly, the coupling member 112', the first and second diversion members 128', 132' and the flexible portions 140', 141' are all capable of having a substantially circular cross-section, which provide a more symmetrical flow of air therethrough versus other shapes such as, for example, square, rectangular, etc.

In some examples, the protective headwear of the present disclosure is capable of providing a high level of comfort to wearers due to the high level of adjustability that accommodates individual wearer's needs and the large variety of environments and conditions in which the protective headwear may be worn. In some examples, this high level of comfort is provided by a low center of gravity due to airflow delivery from the lateral sides of the protective headwear (e.g., lower half of the protective headwear) and a high level of adjustability of one or more of the airflow velocity, airflow direction, and the air flow contacting the key locations on a user's head/face, which may be comprised of those locations of the face with the highest concentration of blood vessels It should be understood that the above examples of the protective headwear and the above examples of the airflow devices are provided for exemplary purpose to demonstrate at least some of the principles of the present disclosure.

Other variants, embodiments, and examples are possible and all of which are intended to be within the spirit and scope of the present disclosure. For example, the protective headwear may be any type of protective headwear and the airflow devices may be coupled to any type of protective headwear including, but not limited to, hard hats, bicycle helmets, military helmets, grinding shields, firefighter helmets, or any other type of protective headwear. Also, for example, the coupling member may include a single duct that couples with a helmet duct, and the helmet duct may divert into multiple helmet ducts to communicate airflow to various locations within the interior of the protective headwear. Further, for example, the coupling member and other components of the airflow device may be coupled to any portion of the protective headwear, not just the headgear. Still further, for example, the airflow device may include any number and type of components to communicate fluid from the air source to the interior of the protective headwear. Additionally, for example, the coupling member may be included as part of the protective headwear by either coupling or unitarily forming the coupling member with the remainder of the protective headwear. Further yet, for example, the manifold or coupling member may divert the airflow into two ducts and the two ducts may extend from the manifold or coupling member all the way to a location where the ducts terminate within the interior of the protective headwear. That is, in this example, the airflow device may be characterized to include only two ducts and the ducts may not be parsed to include various portions as described in the above example. Moreover, it should be understood that the present disclosure is intended to include any number of ducts, tubes, etc., between the manifold or coupling member and a final termination location for conveying air from the manifold or coupling member to the final destination.

It should also be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear and airflow device may be utilized in any orientation and use of such terms is intended to correspond to the exemplary orientation of the protective headwear and airflow device illustrated in the drawings. The use of these terms in association with the protective headwear and airflow device is not intended to limit the protective headwear and airflow device to a single orientation or to limit the protective headwear and airflow device in any manner.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A protective headwear comprising:
   a headgear configured to engage a wearer's head and at least partially support the protective headwear on the wearer's head, wherein the headgear includes a front, a rear opposite the front, a right side, and a left side opposite the right side;
   an outer shell coupled to the headgear at a coupling location about which the outer shell is rotatable, wherein the outer shell includes a shield positioned to the front of the headgear;
   a pair of ducts coupled to and at least partially positioned in an interior of the outer shell; and
   a manifold positioned to the rear of the headgear and configured to divert and receive airflow into each duct of the pair of ducts, wherein each duct of the pair of ducts includes a plurality of exhaust ports configured to exhaust airflow onto locations of a wearer's face, at least one of the exhaust ports on each duct of the pair of ducts being fixed with respect to each duct of the pair of ducts and positioned to exhaust air from at least a top-facing surface of each duct of the pair of ducts in at least an upward direction;
   wherein each duct of the pair of ducts comprises a shell portion coupled to an interior surface of the outer shell and a flexible portion coupled to and between the shell portion and the manifold to provide one of first and second portions of airflow from the manifold to the shell portion of the duct,
   wherein the flexible portion of each duct of the pair of ducts extends from the manifold towards the outer shell and connects to the outer shell at a portion of the protective headwear below the coupling location, and
   wherein the at least one fixed exhaust port on each duct of the pair of ducts is located below the coupling location at which the outer shell is rotatably coupled to the headgear.

2. The protective headwear of claim 1, wherein the manifold includes:
   a first diversion member configured to divert the first portion of airflow; and
   a second diversion member configured to divert the second portion of airflow;
   wherein one of the first and second diversion members is in fluid communication with each duct of the pair of ducts to provide one of the first and second portions of airflow to each duct of the pair of ducts.

3. The protective headwear of claim 1, wherein the shell portion and the flexible portion of each duct of the pair of ducts are positioned completely below the coupling location.

4. The protective headwear of claim 1, wherein the flexible portion of each duct of the pair of ducts is circular or oval in a plane perpendicular to a longitudinal extent of the flexible portion of each duct of the pair of ducts.

5. The protective headwear of claim 1, wherein the pair of ducts includes a first duct and a second duct, wherein the first duct is coupled to a first side of an interior surface of the outer shell and at least partially extending along the first side, and wherein the second duct is coupled to a second side of the interior surface of the outer shell below the coupling location and at least partially extending along the second side, wherein the second side is opposite the first side; and wherein the manifold is coupled to and in fluid communication with both the first and second ducts to provide the first portion of airflow to the first duct and the second portion of airflow to the second duct.

6. The protective headwear of claim 5, wherein the shell portion and the flexible portion of each duct of the pair of ducts are all positioned completely below the coupling location.

7. The protective headwear of claim 5, wherein the flexible portion of each duct of the pair of ducts is circular or oval in respective planes perpendicular to respective longitudinal extents of the flexible portion of each duct of the pair of ducts.

8. The protective headwear of claim 1, wherein the plurality of exhaust ports are configured to exhaust airflow onto locations of a wearer's face having highest concentrations of blood vessels.

9. The protective headwear of claim 8, wherein at least one of direction and velocity of airflow exhausted from the plurality of exhaust ports is adjustable.

10. A protective headwear comprising:
a headgear configured to engage a wearer's head and at least partially support the protective headwear on the wearer's head, wherein the headgear includes a front, a rear opposite the front, a right side, and a left side opposite the right side;
an outer shell coupled to the headgear at a coupling location and including a shield positioned to the front of the headgear;
an airflow device including a pair of ducts coupled to and at least partially positioned in an interior of the outer shell, wherein the pair of ducts include a plurality of exhaust ports configured to exhaust airflow onto locations of the wearer's face, at least one of the exhaust ports on each duct of the pair of ducts being fixed with respect to each duct of the pair of ducts and positioned to exhaust air from at least a top surface of each duct of the pair of ducts in at least an upward direction;
a coupling member coupled to and between the headgear and the airflow device; and
a pair of flexible portions which extend from a manifold toward the outer shell and connect to the outer shell below the coupling location,
wherein the at least one of the exhaust ports on each duct is located below the coupling location at which the outer shell is coupled to the headgear.

11. The protective headwear of claim 10, wherein the manifold is in fluid communication with each duct of the pair of ducts and positioned to the rear of the headgear, wherein the manifold is configured to divert airflow into at least a first portion of airflow and a second portion of airflow, and wherein the coupling member is coupled to and between the headgear and the manifold.

12. The protective headwear of claim 11, wherein the headgear further includes an adjustable member configured to adjust a size of the headgear, wherein the coupling member is coupled to and between the adjustable member and the manifold.

13. The protective headwear of claim 12, wherein the coupling member includes a first closed loop wrapped around the manifold and a second closed loop wrapped around the adjustable member.

14. The protective headwear of claim 10, wherein the coupling member is an elastic coupling member.

15. A protective headwear comprising:
an outer shell including an interior surface;
a first shell duct coupled to the interior surface of the outer shell and including a first exhaust port;
a second shell duct coupled to the interior surface of the outer shell and spaced-apart from the first shell duct, wherein the second shell duct includes a second exhaust port;
a manifold positioned externally of the outer shell and including a first diversion member and a second diversion member, wherein the first and second diversion members are configured to divert airflow into at least a first portion of airflow and a second portion of airflow;
a first flexible duct coupled to and between the first shell duct and the first diversion member to provide the first portion of airflow from the first diversion member to the first shell duct, wherein the first flexible duct is circular or oval along a plane perpendicular to a longitudinal extent of the first flexible duct; and
a second flexible duct coupled to and between the second shell duct and the second diversion member to provide the second portion of airflow from the second diversion member to the second shell duct,
wherein the second flexible duct is substantially circular along a plane perpendicular to a longitudinal extent of the second flexible duct,
wherein the first and second flexible ducts are coupled to the outer shell below a coupling location at which the outer shell is coupled to a headgear,
wherein the first and second shell ducts include at least one or more additional exhaust ports configured to exhaust airflow onto locations of a wearer's face,
wherein at least one of the first, second, or additional exhaust ports on each duct being fixed with respect to the duct and positioned to exhaust air from at least a top surface of the duct
in at least an upward direction, and
wherein the at least one of the first, second, or additional exhaust ports on each duct is located below the coupling location at which the outer shell is coupled to the headgear.

16. The protective headwear of claim 15, wherein the first flexible duct is circular or oval along an entire length thereof, and wherein the second flexible duct is substantially circular along an entire length thereof.

17. The protective headwear of claim 15, wherein:
the first shell duct has a first portion that is circular or oval and a second portion that is non-circular, wherein the first flexible duct is coupled to the first portion of the first shell duct, and wherein the second duct of the first shell duct extends along the interior surface of the outer shell and defines the first exhaust port through which the first portion of airflow exhausts; and
the second shell duct has a first portion that is circular or oval and a second portion that is non-circular, wherein the second flexible duct is coupled to the first portion of the second shell duct, and wherein the second portion of the second shell duct extends along the interior surface of the outer shell and defines the second exhaust port through which the second portion of airflow exhausts.

18. The protective headwear of claim 17, wherein the first exhaust port is one of a plurality of exhaust ports defined in the second portion of the first shell duct, and wherein the second exhaust port is one of a plurality of exhaust ports defined in the second portion of the second shell duct.

19. A protective headwear comprising:
an outer shell including an interior surface, wherein the interior surface has a first side, a second side opposite the first side, a front between the first and second sides, and a top between the first and second sides; and
a duct coupled to and extending along the first side of the interior surface of the outer shell,
wherein the duct includes an inlet through which air is configured to be introduced into the duct, a fixed exhaust port positioned to exhaust air from at least a top surface of the duct in at least an upward direction, the fixed exhaust port being fixed with respect to the duct, and an adjustable exhaust port through which air is configured to be exhausted from the duct and into an interior of the outer shell,
wherein the adjustable exhaust port is positioned along the first side of the interior surface, and wherein the adjustable exhaust port is adjustable between a plurality of positively secured positions to exhaust air therefrom in a plurality of directions, and a pair of flexible duct portions which extend from a manifold toward the outer shell and connect to the outer shell below a coupling location at which the outer shell is coupled to a headgear, wherein the fixed exhaust port and the adjustable exhaust port are both located below the coupling location.

20. The protective headwear of claim 19, wherein the adjustable exhaust port comprises an aperture defined in the duct and a baffle positioned in the aperture, wherein the baffle is movable within the aperture relative to the duct.

21. The protective headwear of claim 20, wherein the baffle is rotatable within the aperture relative to the duct.

22. The protective headwear of claim 20, wherein the duct includes a first securement feature and the baffle includes a second securement feature, wherein the first and second securement features are engageable with each other to positively secure the baffle relative to the duct.

23. The protective headwear of claim 22, wherein the first securement feature is positioned adjacent the aperture defined in the duct and the second securement feature is positioned on a perimeter of the baffle.

24. The protective headwear of claim 22, wherein the first securement feature is a projection and the second securement feature is a plurality of recesses defined in the baffle, wherein the projection is selectively positioned in one of the plurality of recesses at a time.

25. The protective headwear of claim 24, wherein the plurality of recesses are defined in a perimeter of the baffle.

26. The protective headwear of claim 24, wherein the first securement feature includes a plurality of projections.

27. The protective headwear of claim 26, wherein the plurality of projections are selectively positioned in a plurality of the plurality of recesses at a time.

28. The protective headwear of claim 20, wherein the interior surface of the outer shell and the duct together define an airflow path including four sides, wherein the interior surface of the outer shell defines one of the four sides of the airflow path and the duct defines three of the four sides of the airflow path, and wherein the aperture is defined in a side of the duct that is opposite the interior surface of the outer shell.

29. The protective headwear of claim 1, wherein the manifold is positioned to the rear of the headgear and configured to divert airflow from an air source into each duct of the pair of ducts.

30. The protective headwear of claim 1, wherein the manifold is positioned at the rear of the headgear and configured to divert a first portion of airflow from an inlet of the manifold, to an outlet of the manifold, and through each duct of the pair of ducts.

31. The protective headwear of claim 1, wherein the at least one fixed exhaust port on each duct of the pair of ducts is located on a top corner edge of the duct, and is configured to exhaust the air in upward and inward directions.

32. The protective headwear of claim 1, wherein the flexible portion of each duct of the pair of ducts extends from the manifold towards the outer shell and connects to the outer shell at a portion of the protective headwear below the coupling location via an engagement member that is external to the outer shell.

33. The protective headwear of claim 1, further comprising an engagement member that is external to the outer shell and configured to engage the flexible portion of each duct of the pair of ducts.

* * * * *